(12) United States Patent
Erwin et al.

(10) Patent No.: US 11,471,480 B2
(45) Date of Patent: *Oct. 18, 2022

(54) COMPOSITIONS AND METHODS COMPRISING GROWTH FACTORS, CHONDROITIN AND GLUCOSAMINE FOR DEGENERATIVE DISC REGENERATION

(71) Applicants: University Health Network, Toronto (CA); Notogen, Inc., Toronto (CA)

(72) Inventors: William Mark Erwin, North York (CA); Bjorn C. J. Eek, Long Beach, CA (US)

(73) Assignees: UNIVERSITY HEALTH NETWORK, Toronto (CA); NOTOGEN, INC., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/358,731

(22) Filed: Jun. 25, 2021

(65) Prior Publication Data

US 2021/0353664 A1 Nov. 18, 2021

Related U.S. Application Data

(63) Continuation of application No. 15/737,096, filed as application No. PCT/CA2016/051291 on Nov. 4, 2016, now Pat. No. 11,141,426.

(60) Provisional application No. 62/252,234, filed on Nov. 6, 2015.

(51) Int. Cl.

| A61K 38/18 | (2006.01) |
|---|---|
| C07K 14/475 | (2006.01) |
| C07K 14/495 | (2006.01) |
| A61K 31/737 | (2006.01) |
| A61K 31/726 | (2006.01) |
| A61K 31/7008 | (2006.01) |
| C07H 5/06 | (2006.01) |
| A61K 9/00 | (2006.01) |
| A61K 47/38 | (2006.01) |
| A61K 9/08 | (2006.01) |
| A61K 47/26 | (2006.01) |
| C08L 5/08 | (2006.01) |
| A61K 47/20 | (2006.01) |
| A61K 47/36 | (2006.01) |
| C07H 3/02 | (2006.01) |
| A61P 19/02 | (2006.01) |
| C08L 1/28 | (2006.01) |

(52) U.S. Cl.
CPC .......... *A61K 31/737* (2013.01); *A61K 9/0019* (2013.01); *A61K 9/08* (2013.01); *A61K 31/7008* (2013.01); *A61K 31/726* (2013.01); *A61K 38/18* (2013.01); *A61K 38/1841* (2013.01); *A61K 47/20* (2013.01); *A61K 47/26* (2013.01); *A61K 47/36* (2013.01); *A61K 47/38* (2013.01); *A61P 19/02* (2018.01); *C07H 3/02* (2013.01); *C07H 5/06* (2013.01); *C07K 14/475* (2013.01); *C07K 14/495* (2013.01); *C08L 5/08* (2013.01); *C08L 1/286* (2013.01)

(58) Field of Classification Search
CPC .. A61K 38/1841; A61K 38/18; A61K 31/737; A61K 31/7008; A61K 9/0019; C07K 14/495; C07K 14/475; A61P 19/02
See application file for complete search history.

(56) References Cited

U.S. PATENT DOCUMENTS

| 5,837,258 | A | * | 11/1998 | Grotendorst | ......... | C12N 5/0655 |
|---|---|---|---|---|---|---|
| | | | | | | 424/198.1 |
| 6,511,958 | B1 | | 1/2003 | Atkinson et al. | | |
| 7,803,787 | B2 | * | 9/2010 | Marcum | .............. | A61K 31/715 |
| | | | | | | 514/62 |
| 7,897,164 | B2 | | 3/2011 | Scifert | | |
| 8,048,865 | B2 | | 11/2011 | Eek | | |
| 11,141,426 | B2 | | 10/2021 | Erwin | | |
| 11,141,427 | B2 | | 10/2021 | Erwin | | |
| 2006/0246105 | A1 | | 11/2006 | Molz et al. | | |
| 2007/0213718 | A1 | | 9/2007 | Trieu | | |
| 2007/0254040 | A1 | | 11/2007 | Scaffidi | | |
| 2010/0112029 | A1 | | 5/2010 | Scifert | | |
| 2011/0150823 | A1 | | 6/2011 | Huang | | |
| 2012/0294898 | A1 | | 11/2012 | Hubbard et al. | | |
| 2013/0178827 | A1 | | 7/2013 | Hwang et al. | | |
| 2018/0169137 | A1 | | 6/2018 | Erwin | | |
| 2019/0350968 | A1 | | 11/2019 | Erwin | | |
| 2021/0315922 | A1 | | 10/2021 | Erwin | | |

FOREIGN PATENT DOCUMENTS

| JP | 2007531557 A | 11/2007 |
|---|---|---|
| JP | 2008517657 A | 5/2008 |
| JP | 2011515418 A | 5/2011 |
| WO | WO 2005/065280 A2 | 7/2005 |

(Continued)

OTHER PUBLICATIONS

U.S. Appl. No. 17/358,736, filed Jun. 25, 2021, William Mark Erwin.
Tran, C. et al., "CCN2 Suppresses Catabolic Effects of Interleukin-1β through α5β1 and αVβ3 Integrins in Nucleus Pulposus Cells," The Journal of Biological Chemistry, Mar. 14, 2014, 289(11), 7374-7387.
Ali, AA et al., "Oral glucosamine increases expression of transforming growth factor β1 (TGFβ1) and connective tissue growth factor (CTGF) mRNA in rat cartilage and kidney: Implications for human efficacy and toxicity," Archives of Biochemistry and Biophysics, 2011, 510(1), 11-18.

(Continued)

*Primary Examiner* — Xiaozhen Xie
(74) *Attorney, Agent, or Firm* — Cooley LLP

(57) ABSTRACT

There is disclosed herein compositions, methods, uses and systems for reducing pain in a patient that emanates from a body area, preferably spine or joint. Methods of treatment or prevention are described for a disease or condition selected from degenerative disc disease, disc injury, pain, arthritis, or suspected arthritis.

29 Claims, 36 Drawing Sheets

(56) References Cited

FOREIGN PATENT DOCUMENTS

| WO | WO 2006/047255 A1 | 5/2006 |
|---|---|---|
| WO | WO 2009/117740 A2 | 9/2009 |
| WO | WO 2010/088775 A1 | 8/2010 |
| WO | WO 2012/143324 A1 | 10/2012 |

OTHER PUBLICATIONS

Alini, et al., "Are animal models useful for studying human disc disorders/degeneration?" Eur. Spine. J, 2008, 17, 2-19.
Artuzi, et al., "Reduction of osteoarthritis severity in the temporomandibular joint of rabbits treated with chondroitin sulfate and glucosamine." PLoS One, Apr. 15, 2020, 15(4):e0231734. doi: 10.1371/journal.pone.0231734.
Bach, FC et al., "The species-specific regenerative effects of notochordal cell-conditioned medium on chondrocyte-like cells derived from degenerated human intervertebral discs," *Eur Cell Mater*, Sep. 21, 2015, 30, 132-146.
Bergknut, et al., "Intervertebral disc degeneration in the dog. Part 1: Anatomy and physiology of the intervertebral disc and characteristics of intervertebral disc degeneration," Vet. J., 2013, 195, 282-291.
Bekeredijan-Ding, et al., "Poke weed mitogen requires Toll-like receptor ligands for proliferative activity in human and murine B lymphocytes," PLoS One, 2012, 7(1):e29806. doi: 10.1371/journal.pone.0029806.
Blaney Davidson, et al., "Connective Tissue Growth Factor/CCN2 Overexpression in Mouse Synovial Lining Results in Transient Fibrosis and Cartilage Damage," Arthritis and Rheumatism, 2006, 54(5), 1653-1661.
Bydon, et al., "Lumbar fusion versus non-operative management for treatment of discogenic low back pain: a systematic review and meta-analysis of randomized controlled trials," J. Spinal. Disord. Tech., 2014, 27, 297-304.
Calamia V. et al., "A pharmacoproteomic study confirms the synergistic effect of chondroitin sulfate and glucosamine," Scientific Reports, 2014, 4(5069).
Cao, et al., "Bone marrow mesenchymal stem cells slow intervertebral disc degeneration through the $NF_{-\kappa}B$ pathway," Spine. J., 2015, 15, 530-538.
Cho, H et al., "Synergistic effect of combined growth factors in porcine intervertebral disc degeneration," Connective Tissue Research, Apr. 2013, 54(3), 181-186. Cho, H et al., "Synergistic effect of combined growth factors in porcine intervertebral disc degeneration", Connective Tissue Research, Apr. 2013, 54(3), 181-186.
Cornejo, et al., "Soluble factors from the notochordal-rich intervertebral disc inhibit endothelial cell invasion and vessel formation in the presence and absence of pro-inflammatory cytokines," Osteoarthritis. Cartilage., 2015, 23, 487-496.
De Vries, et al., "Conditioned medium derived from notochordal cell-rich nucleus pulposus tissue stimulates matrix production by canine nucleus pulposus cells and bone marrow-derived stromal," Cells. Tissue. Eng. Part. A., 2015, 21, 1077-1084.
Erwin, WM et al., "Nucleus pulposus notochord cells secrete connective tissue growth factor and up-regulate proteoglycan expression by intervertebral disc chondrocytes", Arthritis and Rheumatism, Dec. 2006, 54(12), 3859-3867.
Erwin, WM et al., "Notochordal cells protect nucleus pulposus cells from degradation and apoptosis: implications for the mechanism of intervertebral disc degeneration," Arthritis Research and Therapy, 2011, 13(6), 1-15.
Foss, et al. "Chondroprotective supplementation promotes the mechanical properties of injectable scaffold for human nucleus pulposus tissue engineering," J Mech Behav Biomed Mater, Jan. 2014, 29, 56-67. doi: 10.1016/j.jmbbm.2013.08.020.
Galbusera, et al., "Ageing and degenerative changes of the intervertebral disc and their impact on spinal flexibility," Eur. Spine. J., 2014, 23, S324-32.

Gantenbein, et al. "Activation of intervertebral disc cells by co-culture with notochordal cells, conditioned medium and hypoxia," BMC Musculoskelet Disord, Dec. 11, 2014, 15(422), doi: 10.1186/1471-2474-15-422.
Global Burden of Disease Study 2013 Collaborators. Global, regional, and national incidence, prevalence, and years lived with disability for 301 acute and chronic diseases and injuries in 188 countries, 1990-2013: a systematic analysis for the Global Burden of Disease Study 2013. Lancet, 2015, 386, 743-800.
Gorth, et al., "IL-1ra delivered from poly(lactic-co-glycolic acid) microspheres attenuates IL-1β-mediated degradation of nucleus pulposus in vitro," Arthritis. Res. Ther., 2012, 14, R179.
Goupille, et al., "Is interleukin-1 a good target for therapeutic intervention in intervertebral disc degeneration: lessons from the osteoarthritic experience," Arthritis. Res. Ther., 2007, 9, 110.
Han, et al., "A simple disc degeneration model induced by percutaneous needle puncture in the rat tail," Spine (Phila Pa 1976). Aug. 15, 2008, 33(18), 1925-1934.
Haschtmann, et al., "BMP-2 and TGF-β3 do not prevent spontaneous degeneration in rabbit disc explants but induce ossification of the annulus fibrosus," Eur Spine J., Sep. 21, 2012, 21(9), 1724-1733.
Henderson, et al., "Postarthroscopy analgesia with bupivacaine. A prospective, randomized, blinded evaluation,." Am J Sports Med, Nov.-Dec. 1990, 18(6), 614-617, doi: 10.1177/036354659001800610.
Hoy, et al., "The global burden of low back pain: estimates from the Global Burden of Disease 2010 study," Ann. Rheum. Dis., 2014, 73, 968-974.
Jacobs, et al., "Glucosamine supplementation demonstrates a negative effect on intervertebral disc matrix in an animal model of disc degeneration," Spine (Phila Pa 1976), May 20, 2013, 38(12), 984-990, doi: 10.1097/BRS.0b013e318286b31e.
Jin, et al., "TGF-β signaling plays an essential role in the growth and maintenance of intervertebral disc tissue," FEBS. Lett, 2011, 585, 1209-1215.
Kandel, et al., "Tissue engineering and the intervertebral disc: the challenges," Eur. Spine. J., 2008, 17, 480-491.
Kennon, et al., "Current insights on use of growth factors as therapy for Intervertebral Disc Degeneration," BioMol Concepts, 2018, 9, 43-52.
Klein, et al., "Biochemical injection treatment for discogenic low back pain: a pilot study," Spine J. May-Jun. 2003, 3(3), 220-226, doi: 10.1016/s1529-9430(02)00669-1.
Korecki, et al., "Notochordal cell conditioned medium stimulates mesenchymal stem cell differentiation toward a young nucleus pulposus phenotype," Stem. Cell. Res. Ther., 2010, 1(18).
Kumar, et al., "Identification and intial characterization of 5000 expressed sequenced tags (ESTs) each from adult human normal and osteoarthritis cartilage cDNA libraries," Osteoarthritis and Cartilage, 2001, 9, 641-653.
Le Maitre, et al. "A preliminary in vitro study into the use of IL-1Ra gene therapy for the inhibition of intervertebral disc degeneration," Int. J. Exp. Pathol., 2006, 87, 17-28.
Le Maitre, et al., "Interleukin-1 receptor antagonist delivered directly and by gene therapy inhibits matrix degradation in the intact degenerate human intervertebral disc: an in situ zymographic and gene therapy study," Arthritis. Res. Ther., 2007, 9, R83.
Masuda, K., "Biological repair of the degenerated intervertebral disc by the injection of growth factors," Eur. Spine J., 2008, 17, 441-451.
Matta, et al., "Small interfering RNA targeting 14-3-3ζ increases efficacy of chemotherapeutic agents in head and neck cancer cells," Mol. Cancer. Ther., 2010, 9, 2676-2688.
Mehrkens, et al., "Canine notochordal cell-secreted factors protect murine and human nucleus pulposus cells from apoptosis by inhibition of activated caspase-9 and caspase-3/7," Evid. Based. Spine. Care. J., 2013, 4, 154-156.
Miller, et al., "Treatment of painful advanced internal lumbar disc derangement with intradiscal injection of hypertonic dextrose," Pain Physician, Apr. 2006, 9(2), 115-121.

(56) References Cited

OTHER PUBLICATIONS

Millward-Sadler, et al., "Regulation of catabolic gene expression in normal and degenerate human intervertebral disc cells: implications for the pathogenesis of intervertebral disc degeneration," Arthritis. Res. Ther., 2009, 11, R65.
Muller, Set et al., "Notochordal cell conditioned medium (NCCM) regenerates end-stage human osteoarthritic articular chondrocytes and promotes a healthy phenotype," Arthritis Research & Therapy, Jun. 2, 2016, 18(125), 1-11.
Murab, et al., "Glucosamine loaded injectable silk-in-silk integrated system modulate mechanical properties in bovine ex-vivo degenerated intervertebral disc model," Biomaterials, Jul. 2015, 55, 64-83, doi: 10.1016/j.biomaterials.2015.03.032.
Nishida, et al., "Modulation of the biologic activity of the rabbit intervertebral disc by gene therapy: an in vivo study of adenovirus-mediated transfer of the human transforming growth factor beta 1 encoding gene," Spine (Phila Pa 1976), 1999, 24, 2419-2425.
Nishida, et al., "Gene therapy approach for disc degeneration and associated spinal disorders," Eur. Spine. J., 2008, 17, 459-466.
Omoto, et al., "Expression and localization of connective tissue growth factor (CTGF/Hcs24/CCN2) in osteoarthritic cartilage," Osteoarthritis and Cartilage, 2004, 12, 771-778.
Pattappa, et al., "Diversity of intervertebral disc cells: phenotype and function," J. Anat., 2012, 221, 480-496.
Peng, et al. "Expression and Role of Connective Tissue Growth Factor in Painful Disc Fibrosis and Degeneration," SPINE, 2009, 34(5), 2009, EI78-182.
Phillips, et al., "Interleukin-1 receptor antagonist deficient mice provide insights into pathogenesis of human intervertebral disc degeneration," Ann. Rheum. Dis., 2013, 72, 1860-1867.
Phillips, et al., "Lumbar spine fusion for chronic low back pain due to degenerative disc disease: a systematic review," Spine (Phila Pa 1976)., 2013, 38, E409-22.
Risbud, et al., "Toward an understanding of the role of notochordal cells in the adult intervertebral disc: from discord to accord," Dev. Dyn., 2010, 239, 2141-2148.
Risbud, MV and Shapiro, IM., "Notochordal cells in the adult intervertebral disc: new perspective on an old question," Crit. Rev. Eukaryot. Gene. Expr., 2011, 21, 29-41.
Risbud, MV and Shapiro, IM., "Role of cytokines in intervertebral disc degeneration: pain and disc content," Nat. Rev. Rheumatol., 2014, 10, 44-56.
Ren, et al., "Adjacent segment degeneration and disease after lumbar fusion compared with motion-preserving procedures: a meta-analysis," Eur. J. Orthop. Surg. Traumatol, 2014, 24, S245-53.
Sakai, D and Andersson, GB., "Stem cell therapy for intervertebral disc regeneration: obstacles and solutions," Nat. Rev. Rheumatol., 2015, 11, 243-256.
Sinclair, et al., "Attenuation of inflammatory events in human intervertebral disc cells with a tumor necrosis factor antagonist. Spine (Phila Pa 1976)," 2011, 36, 1190-1196.
Singh, et al., "Animal models for human disc degeneration," Spine. J., 2005, 5, 267S-279S.
Sivan, et al., "Biochemical composition and turnover of the extracellular matrix of the normal and degenerate intervertebral disc," Eur. Spine. J., 2014, 23, S344-53.
Smith, et al. "Degeneration and regeneration of the intervertebral disc: lessons from development." Dis Model Mech, Jan. 2011, 4(1), 31-41. doi: 10.1242/dmm.006403.
Smolders, et al., "Intervertebral disc degeneration in the dog. Part 2: chondrodystrophic and non-chondrodystrophic breeds," Vet. J., 2013, 195, 292-299.
Studer, et al., "p38 MAPK inhibition in nucleus pulposus cells: a potential target for treating intervertebral disc degeneration," Spine (Phila Pa 1976), 2007, 32, 2827-2833.

Tolonen, et al., "Growth factor expression in degenerated intervertebral disc tissue. An immunohistochemical analysis of transforming growth factor beta, fibroblast growth factor and platelet-derived growth factor," Eur. Spine. J., 2006, 15, 588-596.
Van Blitterswijk, et al., "Glucosamine and chondroitin sulfate supplementation to treat symptomatic disc degeneration: biochemical rationale and case report," BMC Complement Altern Med. Jun. 2003, 10;3:2. doi: 10.1186/1472-6882-3-2.
Vergroesen, et al., "Mechanics and biology in intervertebral disc degeneration: a vicious circle," Osteoarthritis. Cartilage., 2015, 23, 1057-1070.
Wang, et al., "Cell and molecular biology of intervertebral disc degeneration: current understanding and implications for potential therapeutic strategies," Cell. Prolif., 2014, 47, 381-390.
Wang, et al., "Enhancing intervertebral disc repair and regeneration through biology: platelet-rich plasma as an alternative strategy," Arthritis. Res. Ther., 2013, 15, 220.
Wang, et al., "Efficacy of intervertebral disc regeneration with stem cells—a systematic review and meta-analysis of animal controlled trials," Gene, 2015, 564, 1-8.
Yang, et al., "TGF-β1 antagonizes TNF-α induced up-regulation of matrix metalloproteinase 3 in nucleus pulposus cells: role of the ERK1/2 pathway," Connect. Tissue. Res., 2015, 29, 1-8.
Yang, H et al., "TGF-β1 Suppresses Inflammation in Cell Therapy for Intervertebral Disc Degeneration," Sci. Rep., Aug. 20, 2015, 5, p. 13254.
Zhang, et al., "Src is a major signaling component for CTGF induction by TGF-β1 in osteoblasts," J Cell Physiol, 2010, 224(3), 691-701.
Liu, et al., "Combined expression of CTGF and tissue inhibitor of metalloprotease-1 promotes synthesis of proteoglycan and collagen type II in rhesus monkey lumbar intervertebral disc cells in vitro," Chin Med J (Engl), 2010, 123:2082-2087.
Walsh, A. J. L. et al., "In vivo growth factor treatment of degenerated intervertebral discs," Spine (Phila Pa 1976). Jan. 15, 2004;29(2):156-63. doi:10.1097/01.BRS.0000107231.67854.9F.
Walsh, A. J. L. et al., "Single and Multiple Injections of Gdf-5, Igf-1, or Tgf-Beta Into Degenerated Intervertebral Discs," 48th Annual Meeting of the Orthopaedic Research Society, 2002; Poster: 0820: 1 page.
Blom, et al., "Gene regulation of connective tissue growth factor: new targets for antifibrotic therapy?" Matrix Biology, 2002, 21:473-482.
Chen, et al., "CTGF expression in mesangial cells: Involvement of SMADs, MAP kinase, and PKC," Kidney International, 2002, 62:1149-1159.
Chen, et al., "TGF-β signaling in intervertebral disc health and disease," Osteoarthritis and Cartilage, 2019, 27:1109-1117.
Ihn, M.D., "Pathogenesis of fibrosis: role of TGF-β and CTGF," Current Opinion in Rheumatology, 2002, 14:681-685.
Qu, et al., "High-dose TGF-β1 degrades human nucleus pulposus cells via ALK1-Smad1/5/8 activation," Experimental and Therapeutic Medicine, 2020, 20:3661-3668.
Rachfal, et al., "Connective tissue growth factor (CTGF/CCN2) in hepatic fibrosis," Hepatology Research, 2003, 26:1-9.
Singh, M.D., et al., "Age-related changes in the extracellular matrix of nucleus pulposus and anulus fibrosus of human intervertebral disc," Spine (Phila Pa 1976), Jan. 1, 2009, 34(1):10-16.
Tolonen, et al., "Transforming growth factor β receptor induction in herniated intervertebral disc tissue: an immunohistochemical study," Eur Spine J., 2001, 10:172-176.
Willems, et al., "Intradiscal application of rhBMP-7 does not induce regeneration in a canine model of spontaneous intervertebral disc degeneration," Arthritis Research & Therapy, 2015, 17(137):1-14.

\* cited by examiner

Fig. 1.
(e)
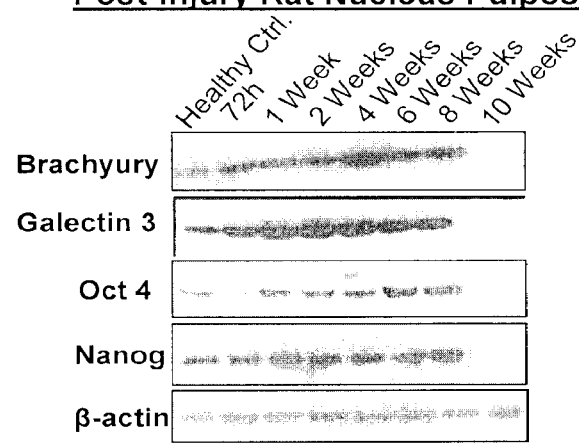
(f)
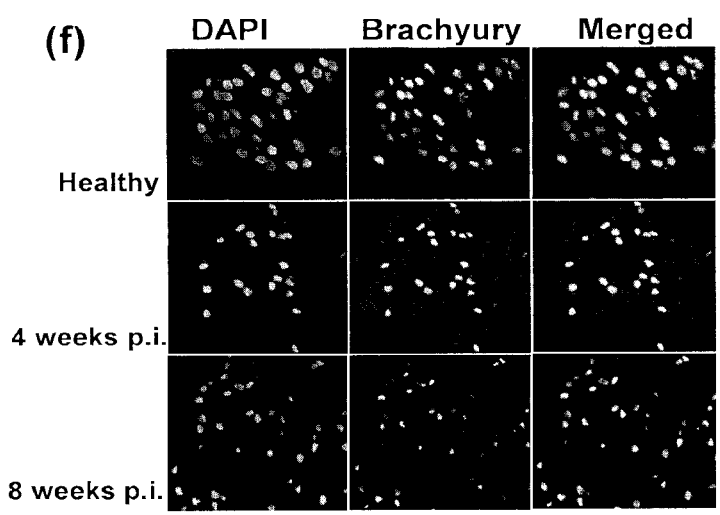
(g)
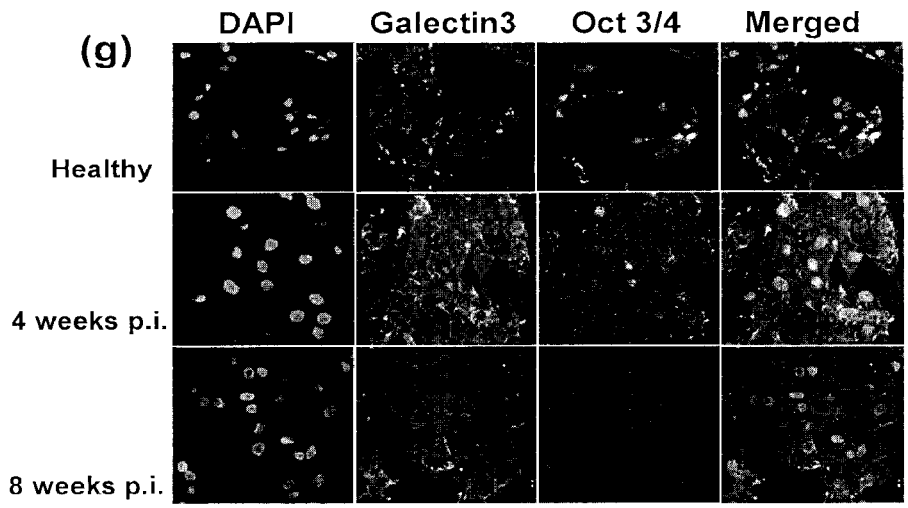

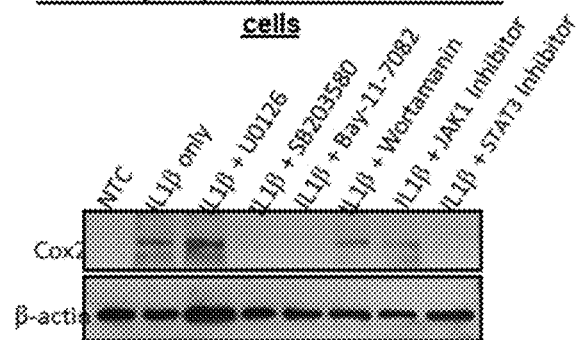
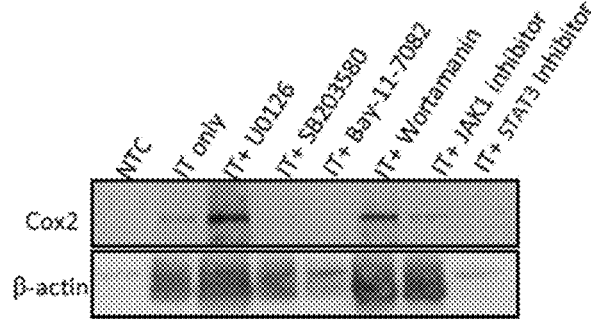
FIG. 2H

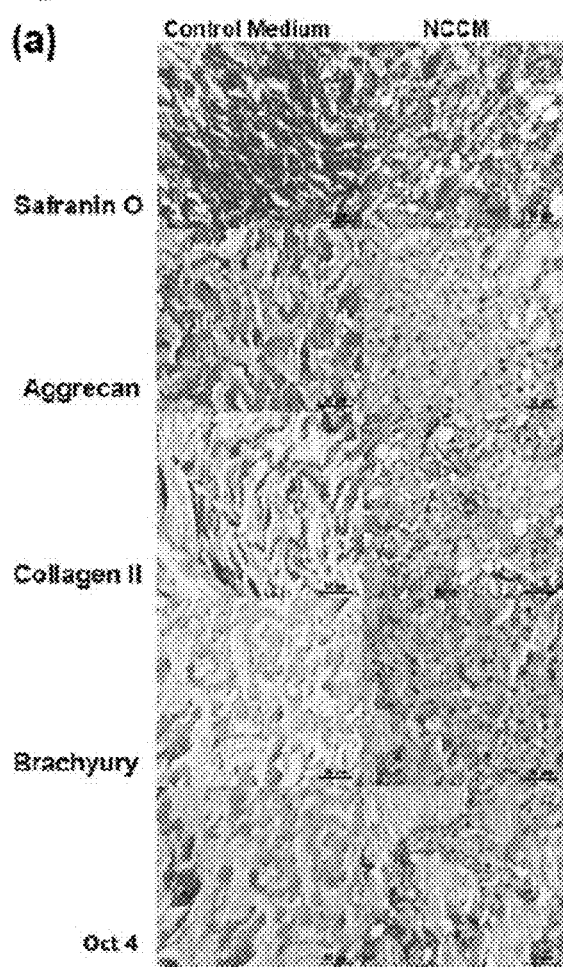

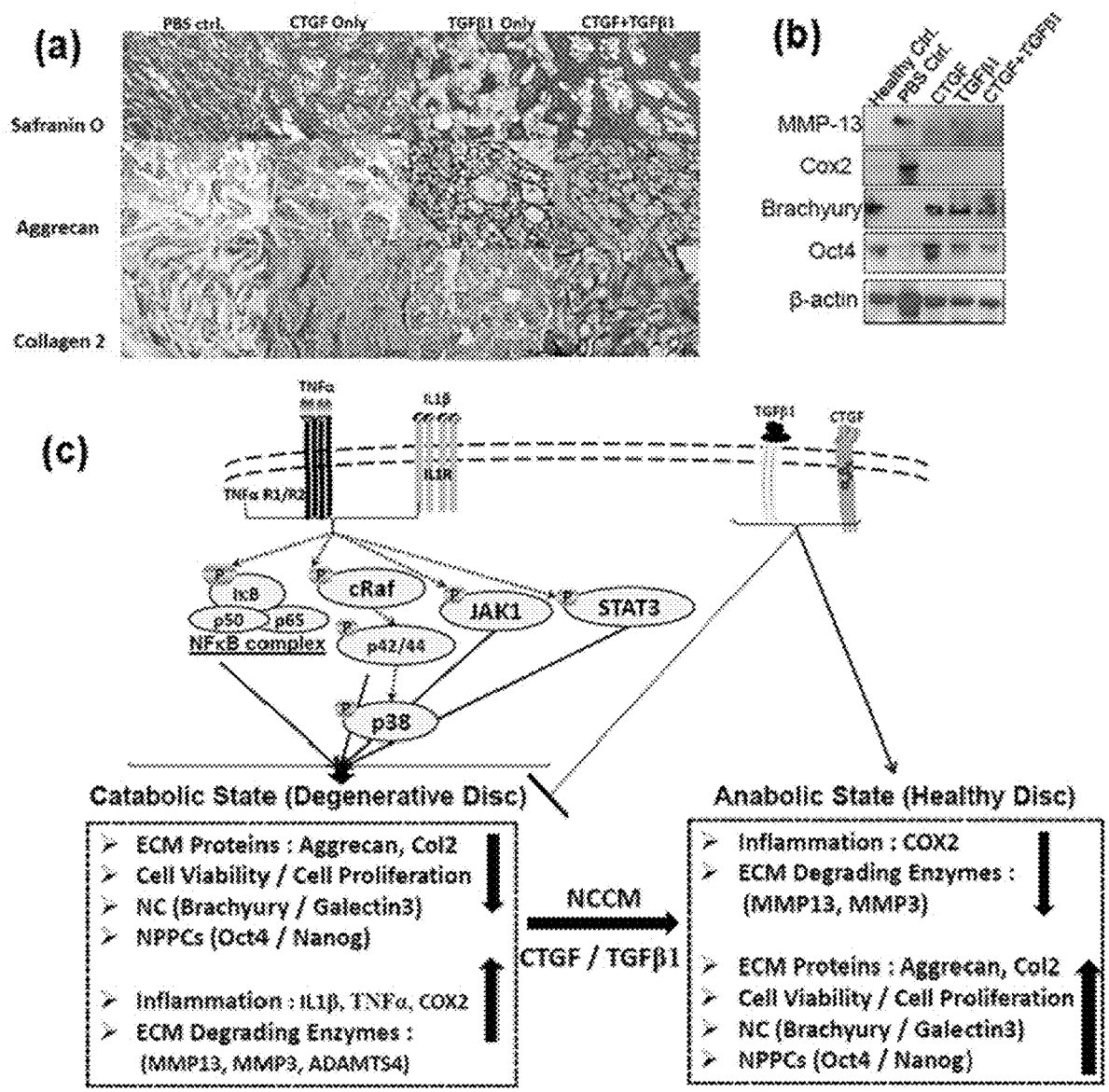

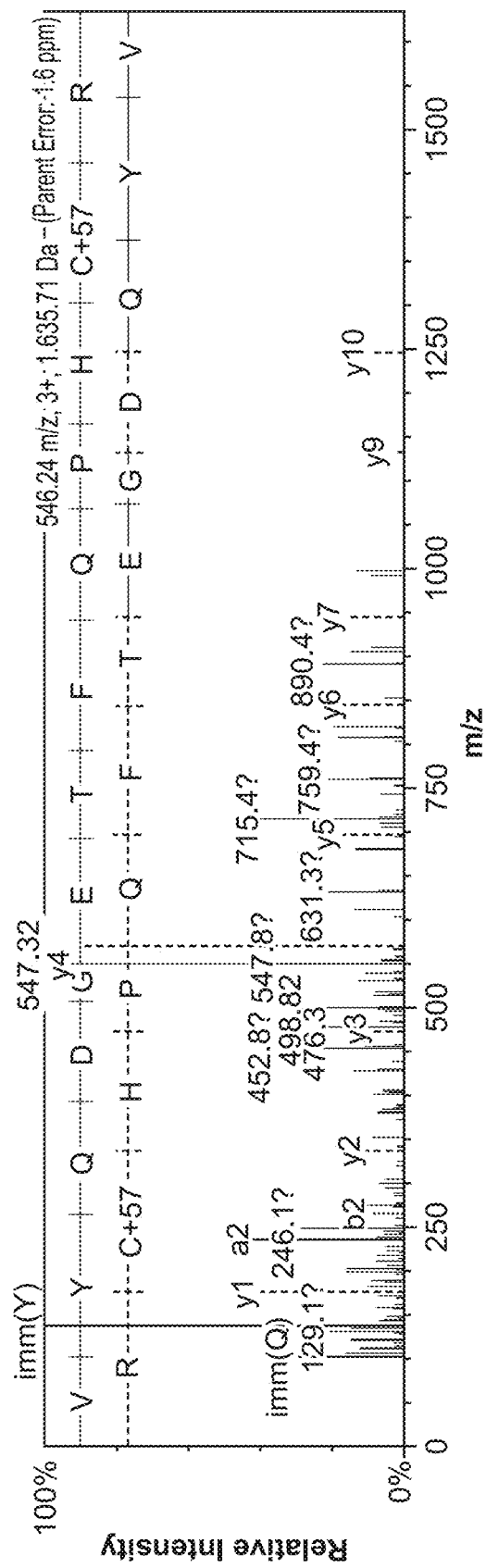
FIG. 9 (Cont. 1)

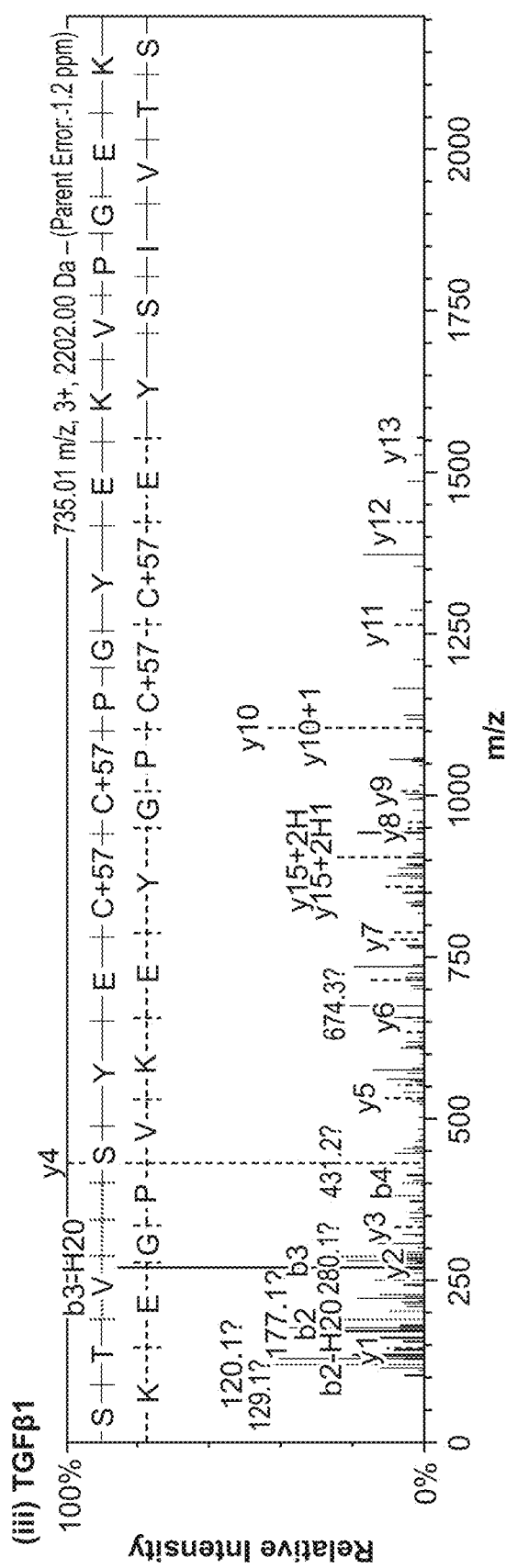
FIG. 9 (Cont. 2)

COMPOSITIONS AND METHODS COMPRISING GROWTH FACTORS, CHONDROITIN AND GLUCOSAMINE FOR DEGENERATIVE DISC REGENERATION

CROSS-REFERENCE TO RELATED APPLICATIONS

This application is a continuation of U.S. application Ser. No. 15/737,096 filed Dec. 15, 2017, now U.S. Pat. No. 11,141,426, which is a U.S. National Phase Entry of PCT Application No. PCT/CA2016/051291 filed Nov. 4, 2016, which claims priority to U.S. Provisional Application No. 62/252,234 filed Nov. 6, 2015, the content of each of which is hereby incorporated by reference in its entirety.

FIELD OF THE INVENTION

This invention relates generally to spinal disc degeneration, and more particularly to methods, inhibitors, uses and systems for treating or preventing disc degeneration.

BACKGROUND OF THE INVENTION

Degenerative disc disease (DDD) is the predominant contributor (~40%) to the genesis of low back pain and is a major cause of disability worldwide, imposing enormous socio-economic burden and clinical costs to the society[1,2]. The healthy intervertebral disc (IVD) is composed of a central proteoglycan rich nucleus pulposus (NP) surrounded by the concentric annulus fibrosus (AF) and attached to the adjacent vertebrae by thin cartilaginous end plates. In humans, large, vacuolated notochordal cells (NCs) present in the NP during childhood are gradually replaced by small chondrocyte-like cells (CLCs) by early adolescence[3-5]. Importantly, there is a temporal relationship between the loss of NCs and the onset of DDD in humans, where degeneration of the NP often leads to compromised disc function, impaired load bearing, associated pain and disability[3-5]. Currently there are no interventions capable of ameliorating the degenerative process or that can promote repair. In fact, surgical procedures such as spinal fusion may hasten adjacent segment degeneration[6-8]. Thus, the development of minimally invasive regenerative therapies is an attractive alternative for disc repair[9-15].

Unlike humans, non-chondrodystrophic canines (NCD) preserve NCs within their NPs and are relatively resistant to DDD[16,17]. Notochordal cell derived conditioned medium (NCCM) obtained from the non-chondrodystrophic canine (NCD) nucleus pulposus confers anabolic characteristics upon NP cells[18-20]. Similarly, other studies have demonstrated increased proteoglycan synthesis and cell proliferation in NP cells treated with NCCM in vitro[21-24]. The reason for apparent beneficial effects upon NCCM treatment has heretofore been unclear, however, and NCCM as a treatment per se has a number of disadvantages, notably including heterogeneity of the mixture.

Therefore, there is a need for an improved treatment for disc degeneration.

SUMMARY OF THE INVENTION

In general, in an aspect, a composition is provided having chondroitin sulfate, present at a level of about 0.1% to about 2.0% by weight; glucosamine hydrochloride, present at a level of about 1% to about 25% by weight; connective tissue growth factor, present at a concentration of about 50 ng/mg of composition to about 500 ng/mg of the composition; transforming growth factor beta 1, present at a concentration of about 10 ng/mg of composition to about 100 ng/mg of the composition; optionally, dextrose, at a level of about 0% to about 25% by weight; optionally, carboxymethylcellulose, at a level of about 0% to about 0.5% by weight and an aqueous solution comprising water and optionally pharmaceutically acceptable carriers, buffer and/or optionally dimethyl sulfoxide, at a collective level equaling the remainder of the composition by weight.

In general, in an aspect, a composition is provided having chondroitin, glucosamine, and a factor selected from connective tissue growth factor, WISP-2, and transforming growth factor beta 1; or pharmaceutically acceptable salts thereof. In one aspect, chondroitin, glucosamine, and either or both of connective tissue growth factor and transforming growth factor beta 1; or pharmaceutically acceptable salts thereof. Implementations may include one or more of the following. The composition also has water. The composition also has dextrose or a pharmaceutically acceptable salt thereof. The composition also has a buffer in quantity sufficient to stabilize the composition pH between about 6 and about 7. The chondroitin is chondroitin sulfate. The chondroitin sulfate is present at a level of about 0.5% to about 2.0%. The chondroitin sulfate is present at a level of about 0.1% to about 0.5%. The glucosamine is glucosamine hydrochloride. The glucosamine hydrochloride is present at a level of about 5% to about 20%. The glucosamine hydrochloride is present at a level of about 1% to about 5%, preferably at a level of about 1.0% to about 1.5% by weight. The composition also has an anesthetic. The anesthetic is bupivacaine. The dextrose is present at a level of up to about 25% by weight. The dextrose is present at a level of about 1% to about 2% by weight. The dextrose is present at a level of about 1.0% to about 1.5% by weight. The connective tissue growth factor (CTGF) is present at a concentration of at least about 50 ng/mL. The CTGF is present at a concentration of at least about 100 ng/mL. The CTGF is present at a concentration of at least about 200 ng/mL. The CTGF is present at a concentration between about 50 and about 500 ng/mL. The transforming growth factor beta 1 (TGFβ1) is present at a concentration of at least about 1 ng/mL. The TGFβ1 is present at a concentration of at least about 5 ng/mL. The TGFβ1 is present at a concentration of at least about 10 ng/mL. The TGFβ1 is present at a concentration between about 1 and about 100 ng/mL. The composition also has pharmaceutically acceptable carriers. The composition also has dimethyl sulfoxide. The composition also has carboxymethylcellulose. The composition also has hyaluronic acid.

In general, in an aspect, a composition is provided having at least one glycosaminoglycan or derivative or precursor thereof, and connective tissue growth factor, and transforming growth factor beta 1; or pharmaceutically acceptable salts thereof. Implementations may include one or more of the following. The glycosaminoglycan is chondroitin. The glycosaminoglycan is glucosamine.

In general, in an aspect, a method of reducing pain in a patient that emanates from a spinal disc is provided, the method including injecting a therapeutically effective amount of one of compositions described above into the disc or into an adjacent disc. Implementations may include one or more of the following. The disc has degenerated. The disc has been previously injured.

In general, in an aspect, a method of treating degenerative disc disease (DDD) or disc injury in a patient is provided, the method including injecting a therapeutically effective amount of one of the compositions described above into the disc or into an adjacent disc.

In general, in an aspect, a method of treating pain, arthritis, or suspected arthritis in a body area of a patient is provided, the method including injecting a therapeutically effective amount of one of the compositions described above into the body area. Implementations may include one or more of the following: the body area is spine; the body area is leg; the body area is a joint: the body area is knee; the body area is a shoulder; the body area is an arm; the body area is an elbow; or the body area is a wrist.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

Embodiments will now be described, by way of example only, with reference to the attached figures, wherein:

FIG. 1 shows Needle puncture injury in rat-tail disc leads to the development of fibrocartilaginous matrix and loss of notochordal (NC) and stem cells in nucleus pulposus (NP). (a) Fluoroscopic image-guided needle puncture injury in rat-tail disc NP. (b) Histological analysis (H&E) and Safranin 0 staining showing development of a fibrocartilaginous matrix over a period of 10 weeks post-injury in rat NP. Immunohistochemistry showing the loss of the ECM proteins, aggrecan and collagen 2 in time dependent manner (healthy to 10 weeks post-injury, Scale bar 50μ). (c) Western blot showing alterations in the expression of pro-inflammatory cytokines (IL-1β and TNFα), inflammation mediator, Cox2 and ECM proteins (MMP-3, MMP-13, TIMP1, ADAMTS4) in a time dependent manner in post-injury rat NP tissue lysates. (d) Western blot of phospho-p42/44 (Thr202/Tyr204), total-p42/44, phospho-p38MAPK (Thr180/Tyr182) and total p38MAPK in tissue lysates obtained from rat tail injured disc NP. (e) Western blot analysis showing loss of NC markers (brachyury, galectin 3) and stem cell markers (Oct4, Nanog) in NPs obtained from rat-tail injured discs over a period of 10 weeks. β-actin was used a loading control in western blots. Immunofluorescence verifying the decrease in (f) nuclear brachyury (g) galectin 3 (membrane/cytoplasm) and nuclear Oct4 expression in rat tail injured discs NPs as compared to healthy control disc NP (Scale bar 10μ).

FIGS. 2a-2h shows IL-1β plays a role in NP-ECM degradation in DDD. Volcano plots depicting differential expression of ECM genes on treatment with (FIG. 2a) IL-1β alone or (FIG. 2b) combination of IL-1β and TNFα, as compared to no treatment controls (NTC) in ECM gene array (n=3, p<0.05). (FIG. 2c) Representative histograms showing significant differential expression (p<0.05) of ECM genes in healthy rat NP cells treated with IL-1β alone, or in combination with TNFα for 24 hrs. (FIG. 2d) Western blots showing IL-1β and TNFα reduced collagen 2, but induced expression of matrix metalloproteinases (MMP-3, MMP-13) and the inflammation mediator, Cox-2 in NP cells obtained from healthy rat IVD-NP. (FIG. 2e) Western blot of phospho-cRaf (Ser259), phospho-p42/44 (Thr202/Tyr204), total-p42/44, phospho-p38MAPK (Thr180/Tyr182) and total-p38MAPK in healthy rat NP cells treated with IL-1β alone or in combination with TNFα for 5-60 minutes. Western blot of MMP-3, MMP-13 and Cox2 in cell lysates obtained from healthy rat NP cells treated with (FIG. 2f) IL-1β alone, (FIG. 2g) combination of IL-1β and TNFα in presence of specific inhibitors targeting p42/44 (U0126), p38MAPK (SB203580), NFκB (BAY-11-7082), PI3K (Wortamanin), Jak1 and STAT3 (WP1066). (FIG. 2h) Western blots showing decreased expression of cytokine induced Cox2 in presence of SB203580, BAY-11-7082, Jak1 and STAT3 (WP1066) inhibitor in human degenerative disc NP cells.

(FIG. 4a) Effect of CTGF, WISP-2 and TGFβ1 treatment alone or in combination on cell viability (72 hrs) as determined using MTT assays in NP cells obtained from (a) rat tail (healthy/injured) discs **p=0.049, *:≤0.02), (FIG. 4b) bovine degenerative disc NPs, *p<0.01 and (FIG. 4c) human (H1-H4) degenerative disc NPs (*p<0.005). Each bar represents mean±S.D. of 3 independent experiments done in triplicates (n=9). Cell proliferation assays (72 hrs) in (FIG. 4d) rat NP cells (healthy/injured discs), *p<0.001, **p<0.01 and (FIG. 4e) human (H1, H2) degenerative disc NPs treated with CTGF and TGFβ1 alone or in combination as determined using colorimetric anti-BrdU-ELISA,*p<0.001. The p-values were determined using paired Student's t-test, for treatment with CTGF, WISP-2 or TGFβ1 alone or in combination with respect to no treatment control (NTC). (FIG. 4f) Histograms showing increased expression of collagen 2, HAPLN1, versican and thrombospondin1 on treatment of human degenerative disc NP cells with CTGF and TGFβ1 as revealed by real time PCR analysis. Each bar in the histogram represents the mean±S.D. of 3 independent experiments done in duplicates (n=6,*p<0.001). (FIG. 4g) Western blot verifying increased collagen 2 expression in human degenerative disc NP cells on treatment with CTGF and TGFβ1.

FIG. 6 shows Evaluation of the regenerative potential of CTGF and TGFβ1 in a pre-clinical in vivo rodent disc injury model of DDD. (a) Representative Safranin-O and immunohistochemical staining of ECM proteins, aggrecan and collagen 2 in paraffin embedded sections of rat tail injured IVD-NPs treated with phosphate-buffered saline (PBS, used as a control), CTGF, TGFβ1 or a combination of CTGF and TGFβ1 (Scale bar 50μ). (b) Western blots showing decreased expression of MMP-13 and Cox2, and restoration of the NC marker, brachyury and stem cell marker, Oct4 in NP tissue lysates obtained from rat tail injured discs treated with CTGF, TGFβ1 or a combination of CTGF and TGFβ1. (c) Proposed model demonstrating the mechanism of progressive disc degeneration in presence of pro-inflammatory cytokines (IL-1β and TNFα) and effect of intervention by potential therapeutic agents (CTGF/TGFβ1) for regeneration of the IVD-NP.

(FIG. 7b) Histological changes in rat disc NP in a time dependent manner (healthy—10 weeks post-injurypost-injury) with hematoxylin and eosin (H&E) staining showing loss of NCs and Safranin-O (SafO) staining showing development of fibrocartilaginous matrix.

(FIG. 8c) Histograms showing caspase 3/7 activity in bovine NP cells treated with etoposide in control medium (serum free, phenol red free Hybridoma Media) or in presence of protein containing fractions (PFs). Each bar represents mean±S.D. of 2 independent experiments done in triplicates (n=6). For these experiments, protein containing fractions (PFs) were mixed (1:1) with control medium (serum free, phenol red free Hybridoma Media) and compared to no treatment controls (i.e. elution buffer+control medium (1:1).

(FIG. 12b) Western blots showing decreased expression of MMP-13 and Cox2, and restoration of the stem cell marker, Oct4 in NP tissue lysates obtained from rat tail injured discs treated with CTGF, TGFβ1, a combination of CTGF and TGFβ1, DRS, DRS in combination with CTGF or a combination of DRS, CTGF and TGFβ1.

DETAILED DESCRIPTION

Figure 2A:
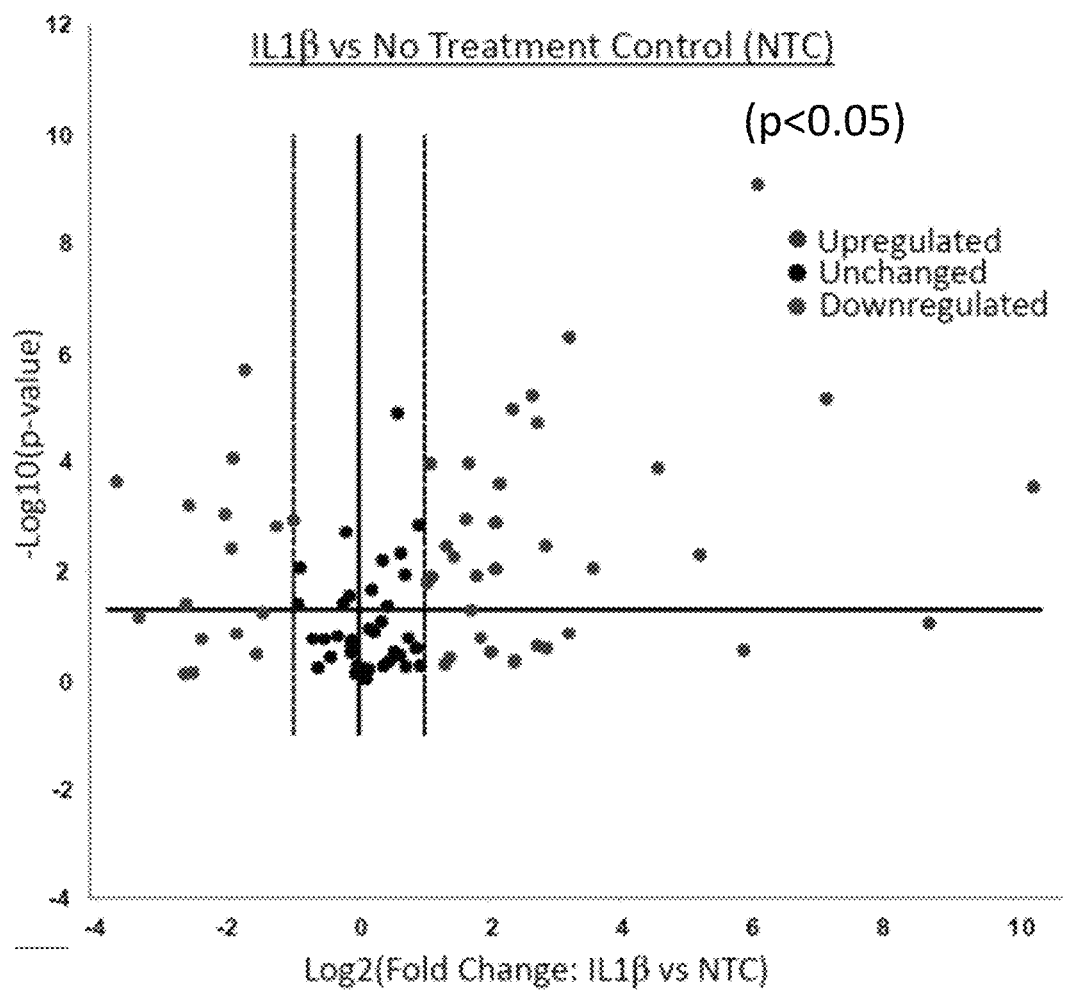

Embodiments of methods, uses, systems, and apparatus suitable for use in implementing the invention are described through reference to the drawings.

In an aspect of the present disclosure, there is provided a composition comprising the following components in aqueous solution, or pharmaceutically acceptable salts thereof: chondroitin (preferably chondroitin sulphate), glucosamine (preferably glucosamine hydrochloride), one or both of connective tissue growth factor (CTGF) and transforming growth factor beta 1 (TGF-beta1), and optionally further comprising dextrose, carboxymethylcellulose, dimethyl sulfoxide, and/or hyaluronic acid.

In some aspects of the present disclosure, treatment comprises administering to the subject a therapeutically effective amount, preferably directly injected at the site in need of therapy.

As used herein, "therapeutically effective amount" refers to an amount effective, at dosages and for periods of time necessary, to achieve the desired therapeutic result. A therapeutically effective amount of the disclosed compositions may vary according to factors such as the disease state, age, sex, and weight of the individual, and the ability of the composition to elicit a desired response in the individual. A therapeutically effective amount is also one in which any toxic or detrimental effects are outweighed by the therapeutically beneficial effects.

Therapeutically effective compositions described herein suitably include at least about 1, 5, 10, 15, 20, 25, 30, 35, 40, 45, 50, 55, 60, 65, 70, 75, 80, 90, 95, or 100 ng/mL TGFβ1, or in a range of about 1 to about 100 ng/mL TGFβ1. Therapeutically effective compositions described herein suitably include at least 50, 75, 100, 125, 150, 175, 200, 225, 250, 275, 300, 325, 350, 375, 400, 425, 450, 475, or 500 ng/mL CTGF, or in a range of about 50 to about 500 ng/mL CTGF. Therapeutic effects were seen in experiments utilizing 1 ng/mL TGFβ1, preferably 5 ng/mL TGFβ1, more preferably 10-100 ng/mL TGFB1; and in experiments utilizing at least about 50 ng/mL CTGF.

Compounds used in the compositions described herein can be used in the form of pharmaceutically acceptable salts derived from inorganic or organic acids. Pharmaceutically acceptable salt(s) are well-known in the art. For clarity, the term "pharmaceutically acceptable salts" as used herein generally refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., Remington's Pharmaceutical Sciences, 18 th ed. (Mack Publishing, Easton Pa.: 1990) and Remington: The Science and Practice of Pharmacy, 19th ed. (Mack Publishing, Easton Pa.: 1995). The preparation and use of acid addition salts, carboxylate salts, amino acid addition salts, and zwitterion salts of compounds used in the compositions described herein may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use.

In one embodiment, there is provided a composition comprising at least one of CTGF and TGF-beta1 and an ECM component. In one embodiment, the at least one ECM component comprises a glycosaminoglycan or derivative or precursor thereof. In one embodiment, the glycosaminoglycan or derivative or precursor thereof comprises chondroitin. In one embodiment, the glycosaminoglycan or derivative or precursor thereof comprises glucosamine. In one embodiment, the composition comprises chondroitin and glucosamine. In one embodiment, the composition comprises CTGF, TGF-beta1, chondroitin and glucosamine.

In one embodiment, the composition further comprises at least one sugar. In one embodiment, the sugar is a cellulose derivative. In one embodiment, the sugar is carboxymethylcellulose. In one embodiment, the sugar is dextrose.

In one embodiment, the composition may comprise a further growth factor. In one embodiment, the further growth factor is WISP-2.

In one aspect, there is provided a composition comprising chondroitin, glucosamine, CTGF, and TGF-β1 or a pharmaceutically acceptable salt thereof. The composition suitably further includes water and dimethyl sulfoxide (DMSO), where the DMSO is up to 15%, up to 10% or preferably under about 5% based on the total composition weight. In one embodiment, the composition is a saline solution. In one embodiment, the composition further comprises dextrose or a pharmaceutically acceptable salt thereof.

In one embodiment, the composition further includes a buffer in a quantity sufficient to stabilize the composition at a desired pH. In one embodiment, the composition is stabilized at a pH between about 6 and about 7.

In one embodiment, the composition comprises chondroitin, preferably chondroitin sulfate.

In one embodiment, chondroitin, preferably chondroitin sulfate, is present at a level of about 0.1% to about 2.0%, in one embodiment, about 0.1% to about 1.0%, in another embodiment, 0.5% to about 2% by weight based on the total composition.

In one embodiment, glucosamine, preferably glucosamine hydrochloride, is present at a level of about 1% to about 25%, in one embodiment about 1% to about 10%, in another embodiment about 5% to about 25% by weight based on the total composition.

In one embodiment, the composition further includes an anesthetic, suitably bupivacaine.

In one embodiment, the composition further includes a contrast agent, in one embodiment, a non-ionic contrast agent.

In one embodiment, dextrose is present at a level of about 25% by weight based on the total composition. In one embodiment, the dextrose is not present. In one embodiment, the dextrose is present at a level of about 5% by weight based on the total composition. In another embodiment, the dextrose is present at a level between about 1% and about 2% by weight based on the total composition.

The CTGF is suitably present in the composition at a concentration of at least about 50 ng/mL of the composition, in one embodiment, at least about 100 ng/mL, in another embodiment, at least about 200 ng/mL, and in one embodiment between about 50 and about 500 ng/mL.

The TGFβ1 is suitably present in the composition at a concentration of at least about 1 ng/mL of the composition, in one embodiment at least about 5 ng/mL, in another embodiment at least about 10 ng/mL, and in another embodiment between about 1 and about 100 ng/mL.

In one embodiment, there is provided a composition that comprises, consists or consists essentially of:
  chondroitin sulfate, present at a level of about 0.1% to about 2.0% by weight;
  glucosamine hydrochloride, present at a level of about 1% to about 25% by weight;
  connective tissue growth factor, present at a concentration of about 50 ng/mg to about 500 ng/mg of the composition;

transforming growth factor beta 1, present at a concentration of about 10 ng/mg to about 100 ng/mg of the composition;

optionally, dextrose, at a level of about 0% to about 25% by weight;

optionally, carboxymethylcellulose, at a level of about 0% to about 0.5% by weight;

and an aqueous solution comprising water and optionally pharmaceutically acceptable carriers, buffer and/or dimethyl sulfoxide, at a collective level equaling the remainder of the composition by weight.

As illustrated in the Examples, compositions as described herein may suitably be used in therapy for disk degeneration or injury.

In one embodiment, there is provided a method of reducing pain in a patient that emanates from a spinal disc, the method comprising injecting a therapeutically effective amount of a composition as described herein into the disc. The disc may be a degenerated disc and/or a previously injured disc.

In one embodiment, there is provided a method of treating DDD or disc injury in a patient comprising injecting a therapeutically effective amount of the composition as described herein into the disc.

While in one embodiment, the timing of treatment is not restricted, in one embodiment, treatment is performed within about 10 weeks following injury, and in other embodiments, within 4 weeks following injury, within 2 weeks following injury or within 96 hours following injury.

In one embodiment, there is provided a method of treating pain, arthritis, or suspected arthritis in a body area of a patient, the method comprising injecting a therapeutically effective amount of the composition described herein into the body area. The body area may be, but is not limited to, the spine or a joint. Other body areas that suitably may be treated according to methods described herein are the shoulder, wrist or elbow.

It will be understood that, where appropriate, treatment may include a prophylactic or preventative treatment, including treatment of an adjacent body area such as in an adjacent disc of the spine.

It will be appreciated by those skilled in the art that other variations of the embodiments described herein may also be practiced without departing from the scope of the invention. Other modifications are therefore possible.

Identified herein are factors secreted by notochordal cells (TGFβ1 and CTGF) that have the capacity to restore a healthy nucleus pulposus by altering the catabolic state of a degenerative intervertebral disc. Also shown, in multiple species including humans, is that the loss of both TGFβ1 and CTGF within the degenerative disc is associated with the development and progression of disc degeneration. The Examples demonstrate the utility of using a combination of TGFβ1 and CTGF in a novel, molecular regenerative therapy for DDD (see for example, FIGS. 4(e), 5(i), and 5(j)). Moreover, there is additional utility in combining TGFβ1 and CTGF with therapeutic and other agents previously identified in U.S. Pat. No. 8,048,865. In an embodiment, these agents comprise chondroitin, glucosamine, and dextrose. In an embodiment, these agents comprise a carrier, such as carboxymethylcellulose and/or hyaluronic acid. In an embodiment, the amount of carboxymethylcellulose present in a composition is less than about 0.5% by weight. The selection of appropriate pharmaceutically acceptable carriers depends on, among other things, the desired dosage form, body area to be impacted, and route of administration.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

EXAMPLES

Proteins present in bioactive fractions of NCCM using liquid chromatography and tandem mass spectroscopy (LC-MS/MS) were identified. The regenerative potential of TGFβ1, CTGF and Wnt-inducible soluble protein-2 (WISP2) identified in NCCM was evaluated using in vitro (rat, bovine and human NP cells) and a pre-clinical rodent model of DDD.

Development of a Preclinical Model of DDD

Figure 7A:
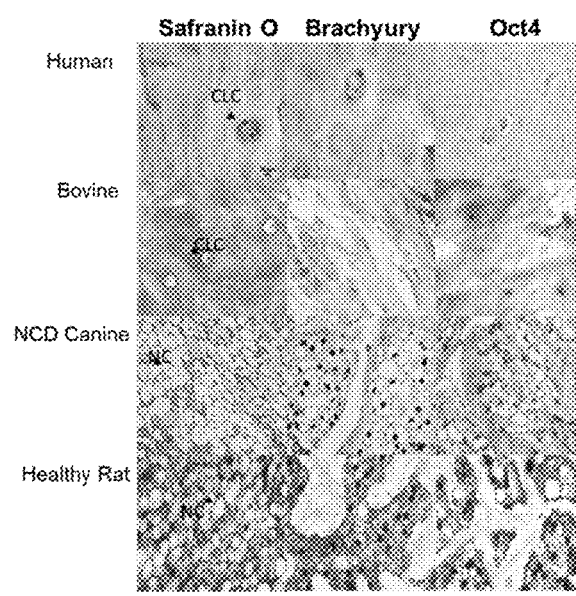
FIGS. 7a-7b shows (FIG. 7a) Safranin 0 staining and immunohistochemical analysis of brachyury and Oct4 proteins in paraffin embedded sections of nucleus pulposus obtained from human degenerative disc, bovine degenerative disc, non-chondrodystrophic canine and healthy rat discs (Scale bar 10μ). Arrows represent CLC, chondrocyte like cells and NC, notochordal cells.

The lack of a well characterized animal model of DDD poses a major challenge for comparative analysis and accurate assessment of potential therapeutic agents. Moreover, response to therapeutic agents are likely to be influenced by differences in histological and phenotypic differences among species[25,26]. In search of an appropriate animal model that mimics human DDD and is suitable for evaluation of therapeutic agents, the histological characteristics of human degenerative disc NP was compared with bovine, NCD canine and Wistar rat IVDs. Strong Safranin-O staining demonstrative of a fibrocartilaginous matrix in NPs obtained from human and bovine degenerative IVDs (FIG. 7a) was observed. In contrast, healthy, notochordal cell-rich non-chondrodystrophic (NCD)—canines and young, healthy Wistar rats have a highly cellular NC-rich NP (>90%) with faint Safranin-O staining (FIG. 7a). Differences in cellular phenotype among NPs were verified using immunohistochemistry for brachyury, a NC-specific marker, and Oct4, a known marker of stem cells[4,5]. Immunohistochemical analysis revealed no detectable expression of brachyury or Oct4 in human or bovine degenerative disc NPs (FIG. 7a). However, strong nuclear expression of brachyury and Oct4 was observed in healthy, young NCD canine and Wistar rat discs confirming the presence of NCs and stem cells within these NPs (FIG. 7a).

Figure 7B:
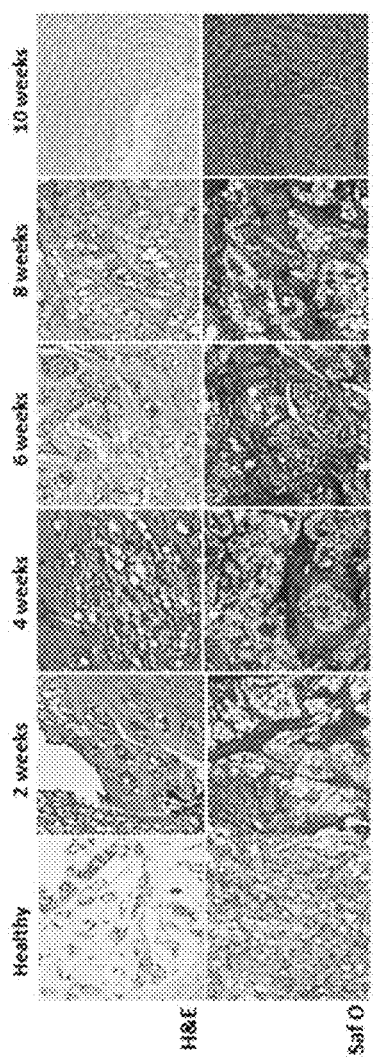

In order to establish a platform for the evaluation of therapeutic agents, a pre-clinical rodent model of DDD was adopted. Image-guided needle puncture injuries were performed in caudal (tail) discs of 12 week-old, healthy Wistar rats (n=21, 4 discs per animal). Changes in the extra-cellular matrix (ECM) and the cellular phenotype were determined in a time dependent manner (72 hrs-10 weeks, FIG. 1a-g). Histological analysis revealed a gradual loss of NCs (>70%) along with increased Safranin-O staining intensity from 2-10 weeks, indicating ECM re-modelling in the NP following injury (FIG. 1b, FIG. 7b). Decreased expression of aggrecan and collagen 2 was also observed by the end of 10 weeks post injury (FIG. 1b). Of note, needle puncture injury increased the expression of the pro-inflammatory cytokines, tumor necrosis factor alpha (TNFα) and interleukin-1 beta (IL-1β) as early as 72 hrs post-injury in NPs (FIG. 1c). However, the active form of IL-1β (~17 kDa) was not observed until 10 weeks, coincident with an abrupt increase in the expression of the inflammation mediator, cyclooxygenase 2 (COX2) and the ECM degrading enzymes, matrix metalloproteinases (MMP-3, MMP-13, FIG. 1c). Interestingly, the loss of tissue inhibitor of metalloproteinases 1 (TIMP1), a natural inhibitor of MMPs was observed at the end of 10 weeks post injury coincident with the onset of MMPs (FIG. 1c). A significant increase in the expression of A disintegrin-like and metalloprotease with thrombospondin type 1 motif 4 (ADAMTS4), one of the major enzymes responsible for aggrecan degradation was observed 1 week post-injury (FIG. 1c). In addition, needle puncture injury also induced phosphorylation of p42/44 (Thr202/Tyr204) and p38MAPK (Thr180/Tyr182) suggesting their role in disc degeneration (FIG. 1d). In parallel, western blotting and immunofluorescence using confocal microscopy demonstrated the loss of the NC markers (brachyury and galectin 3) and stem cell markers (Oct4 and Nanog) in the injured disc NPs, 10 weeks post-injury (FIG. 1e-g). These findings clearly demonstrated a shift in the NP milieu from a healthy, homeostatically regulated environment to a pro-inflammatory, catabolic state with loss of both NCs and stem cells in the degenerative disc.

Regulation of ECM Turnover in DDD

Figure 2B:
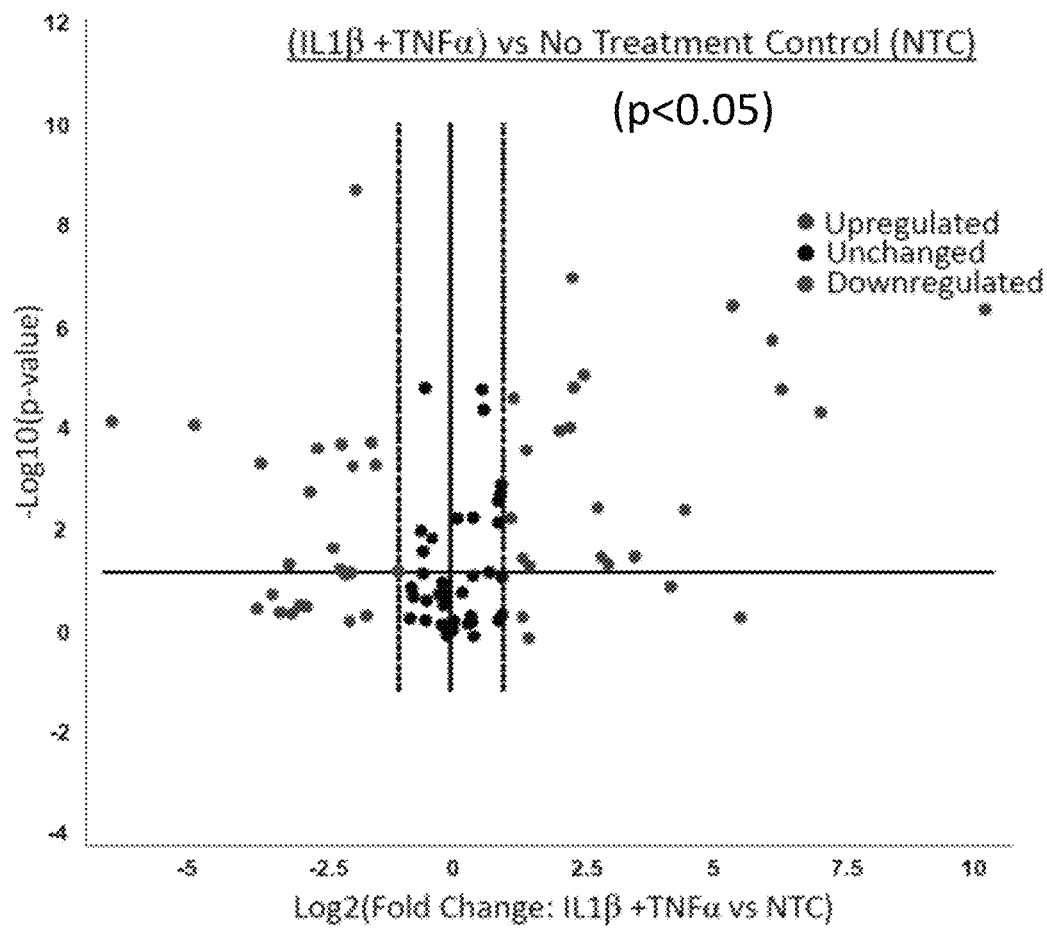
Figure 2C:
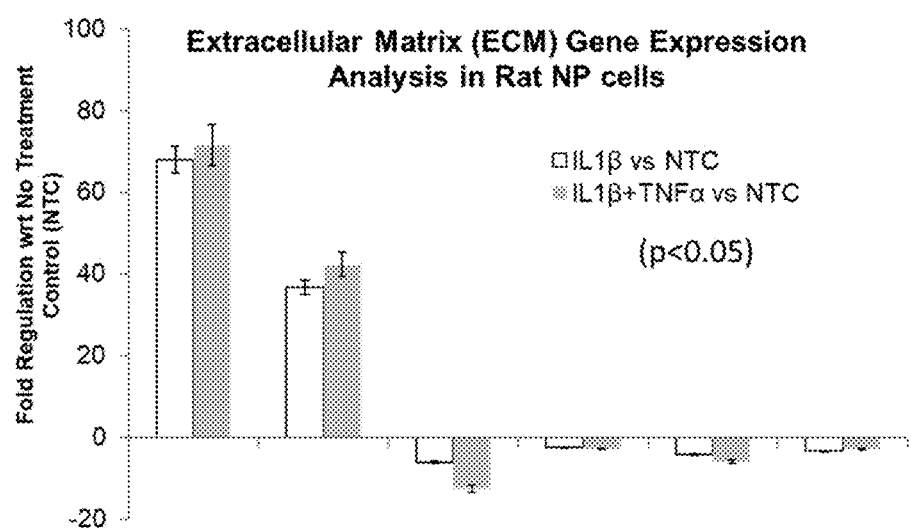

Unlike the hydrophilic, proteoglycan rich ECM seen in healthy NPs, the degenerative disc microenvironment is catabolic, rich in pro-inflammatory cytokines (IL-1β and TNFα) and reflects a failure of homeostasis as demonstrated in the rat-tail disc injury model. To determine the effect of IL-1β and TNFα on ECM turnover, rat NP cells were treated with IL-1β alone or in combination with TNFα for 24 hrs and real time quantitative PCR was performed using the ECM and cell adhesion molecule gene arrays (includes 84 genes). Treatment of rat NP cells with IL-1β alone or in combination with TNFα showed significant changes ($p<0.05$) in the expression of 22 mRNA transcripts including downregulation of healthy matrix genes (HAPLN1, CTGF, Thrombospondin 1 and 2) and upregulation of matrix degrading enzymes, MMPs (MMP-3/9/11/13) as compared to no treatment controls (NTC, FIG. 2a-c, Table 1):

TABLE 1

List of Extra-cellular Matrix (ECM) Genes showing Upregulation/Downregulation on treatment with IL1beta alone/combination of IL1beta + TNFalpha w.r.t No treatment Control (NTC)

| Gene Symbol | Fold regulation (IL1β vs NTC) | p-value | Fold regulation (IL1β + TNFα vs NTC) | p-value |
|---|---|---|---|---|
| MMP9 | 1252.77 | 0.000 | 1216.76 | 0.000 |
| Adamts8 | 139.39 | 0.000 | 81.95 | 0.000 |
| MMP3 | 68.04 | 0.000 | 71.56 | 0.000 |
| MMP13 | 36.82 | 0.005 | 42.39 | 0.000 |
| Cd44 | 23.57 | 0.000 | 22.48 | 0.003 |
| Itga3 | 9.22 | 0.000 | 7.04 | 0.003 |
| Icam1 | 6.56 | 0.000 | 5.84 | 0.000 |
| Itga5 | 6.23 | 0.000 | 8.12 | 0.034 |
| Timp1 | 5.04 | 0.000 | 5.02 | 0.000 |
| Emilin1 | 4.42 | 0.000 | 4.87 | 0.000 |
| Col4a1 | 4.24 | 0.001 | 5.12 | 0.000 |
| Lamc1 | 4.24 | 0.009 | 4.25 | 0.000 |
| Col4a2 | 3.20 | 0.000 | 2.75 | 0.000 |
| Itgav | 2.14 | 0.000 | 2.22 | 0.004 |
| Cdh3 | −6.18 | 0.410 | −8.58 | 0.035 |
| Hapln1 | −6.01 | 0.001 | −12.59 | 0.000 |
| Thbs2 | −4.14 | 0.001 | −5.90 | 0.000 |
| Mmp11 | −3.86 | 0.004 | −6.51 | 0.001 |
| Col3a1 | −3.80 | 0.000 | −3.53 | 0.000 |
| Thbs1 | −3.35 | 0.000 | −2.87 | 0.000 |
| Ctgf | −2.40 | 0.001 | −2.71 | 0.000 |
| Ncam1 | −2.00 | 0.001 | −3.68 | 0.000 |

Figure 2D:
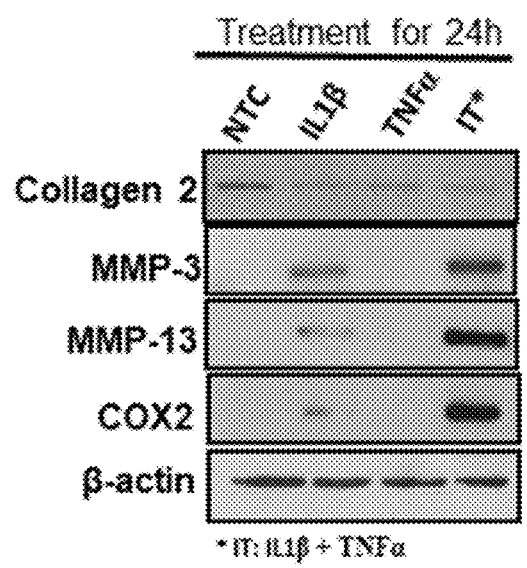
Figure 2E:
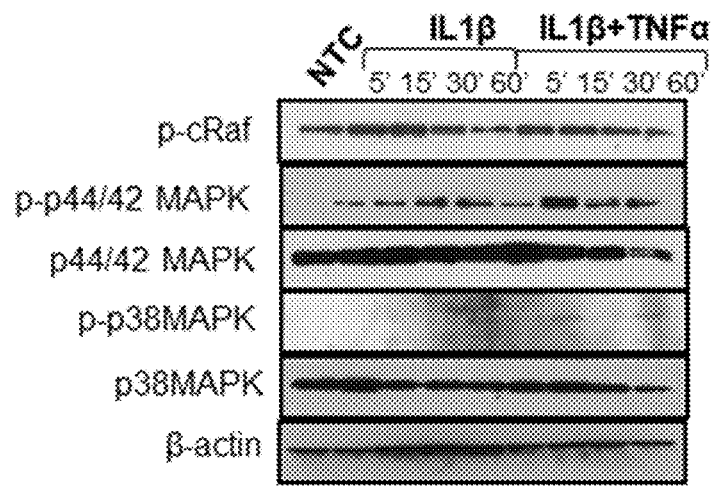

Western blotting verified a marked increase in MMP-3 and MMP-13 expression levels in rat NP cells treated with IL-1β and TNFα (FIG. 2d). In addition, an increase in Cox2 but decreased Collagen 2 expression in rat NP cells was also observed in response to IL-1β and TNFα treatment (FIG. 2d).

Figure 2F:
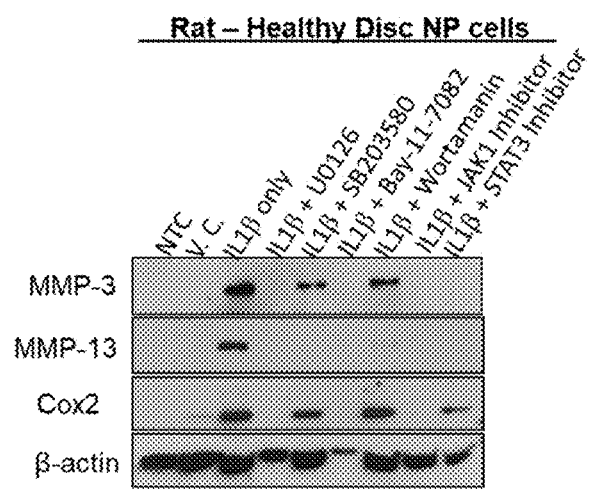
Figure 2G:
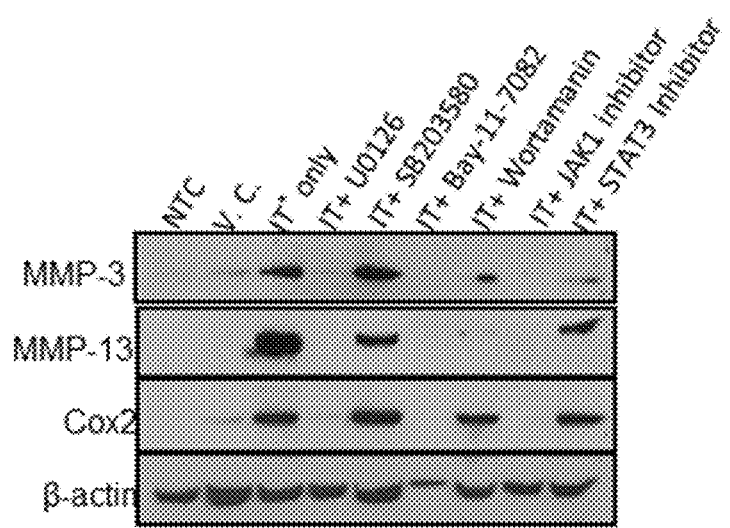

Notably, IL-1β or its combination with TNFα increased phosphorylation levels of c-Raf (S259), p42/44 (Thr202/Tyr204) and p38MAPK (Thr180/Tyr182) without any significant change in their total protein content (FIG. 2d,e). Both IL-1β and TNFα failed to induce MMP-3, MMP-13 or Cox2 expression in presence of U0126, a specific inhibitor of p42/44MAPK in rat NP cells (FIG. 2f, g). In the presence of p38MAPK inhibitor, SB203580, reduced expression of MMP-3, MMP-13 and Cox2 was observed in IL-1β treated rat NP cells (FIG. 2f). These observations support in vivo data suggesting that the activation of p42/44 and p38MAPK downstream of IL-1β and TNFα are important in the regulation of ECM proteins during disc degeneration (FIG. 1d). The results obtained also suggest the involvement of nuclear factor kappa B (NFκB), Jun activated kinase 1 (JAK1), and the signal transducer and activation of transcription 3 (STAT3) in IL-1β and TNFα induced MMP-3, MMP-13 and Cox2 expression in NP cells. Reduced expression of MMP-3, MMP-13 and Cox2 proteins was shown in rat NP cells treated with IL-1β and TNFα in the presence of BAY-11-7082 (NFκB inhibitor) JAK1 or STAT3 specific inhibitor (FIG. 2f, g). In contrast, presence of Wortamanin (PI3K inhibitor) reduced expression of MMP-3 and MMP-13 only (FIG. 2f, g). Similarly, in NP cells obtained from human degenerative discs, IL-1β and TNFα failed to induce Cox2 in presence of inhibitors of p38MAPK, NFκB, JAK1 or STAT3 (FIG. 2h). These findings suggested the importance of p38MAPK, NFκB, JAK1 and STAT3 proteins in progressive disc degeneration.

NCCM Promotes ECM Turnover and Reduces In Vivo Inflammation

Figure 3:
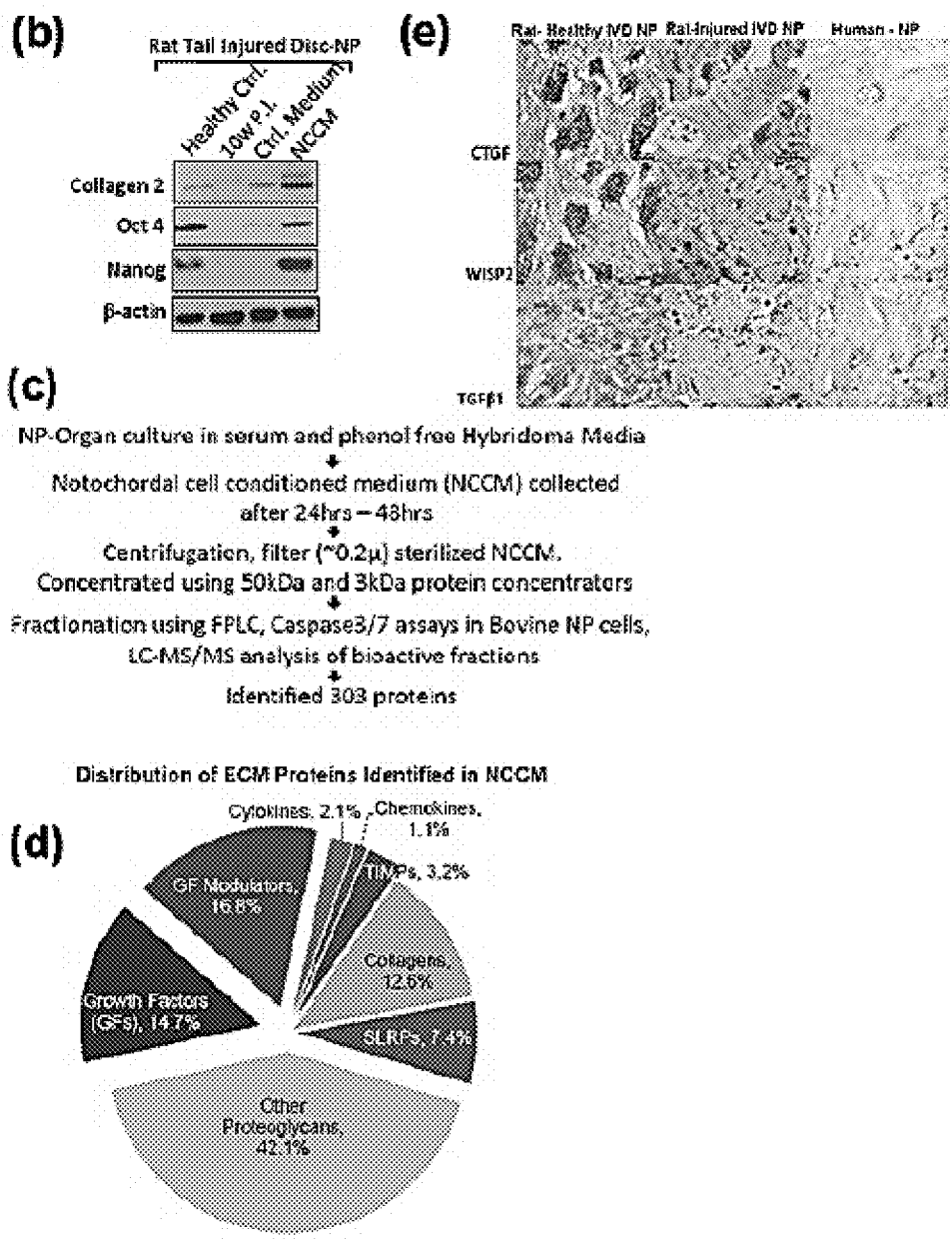
FIG. 3 shows NCCM confers anabolic and anti-catabolic characteristics to degenerating NP in rat-tail injured IVD-NP. (a) Safranin 0 staining showing alteration from the normal plentiful and large notochordal cell, proteoglycan-rich ECM to one largely devoid of notochordal cells replaced by small NP cells. Immunohistochemistry of aggrecan, collagen 2, brachyury and Oct4 in paraffin embedded sections of rat-tail injured discs treated with protein free Hybridoma medium used as control or NCCM (Scale bar 50μ). (b) Western blot of collagen 2 and the stem cell markers Oct4 and Nanog in tissue lysates obtained from rat-tail injured disc NPs and healthy controls. (c) Schematic representation of the methodology for identification of proteins in NCCM using mass-spectroscopy. (d) Pie-chart showing distribution of ECM proteins identified in NCCM. (e) Immunohistochemistry showing expression of CTGF, WISP-2 and TGFβ1 in paraffin-embedded sections of rat NP (healthy and injured discs) and human degenerative disc NP.

The present inventors previously demonstrated that conditioned medium derived from notochordal cells (NCCM) showed anti-apoptotic effects, and induced upregulation in aggrecan and collagen 2 mRNA levels in vitro[19,20]. However, the regenerative potential of NCCM in a pre-clinical in vivo model of DDD had not been evaluated. NCCM was collected by placing NC-rich NPs obtained from NCD-canines in phenol red free, serum free Hybridoma media and harvested conditioned medium according to previously described protocols[18-2]. Concentrated NCCM or control medium (~8 μL/disc) was injected into the injured (4 week post-injury) rat-tail disc NPs using fluoroscopic imaging. Ten weeks post-injury, histological analysis revealed NC-rich NPs with moderate Safranin-O staining in NCCM injected rat-tail injured discs (FIG. 3a). In contrast, rat-tail injured discs injected with control medium showed low cellularity and displayed a fibrocartilaginous matrix, with intense Safranin-O staining, demonstrative of fibrocartilaginous morphology (FIG. 3a). Immunohistochemistry and western blotting revealed the restoration of aggrecan, collagen 2, brachyury, Oct4 and Nanog in rat-tail injured discs injected with NCCM in comparison to sham controls (FIG. 3a, b). These results demonstrated that soluble factors within NCCM have regenerative potential for DDD in vivo.

Identification of Soluble Factors in NCCM Using Mass Spectroscopy

Figure 8A:
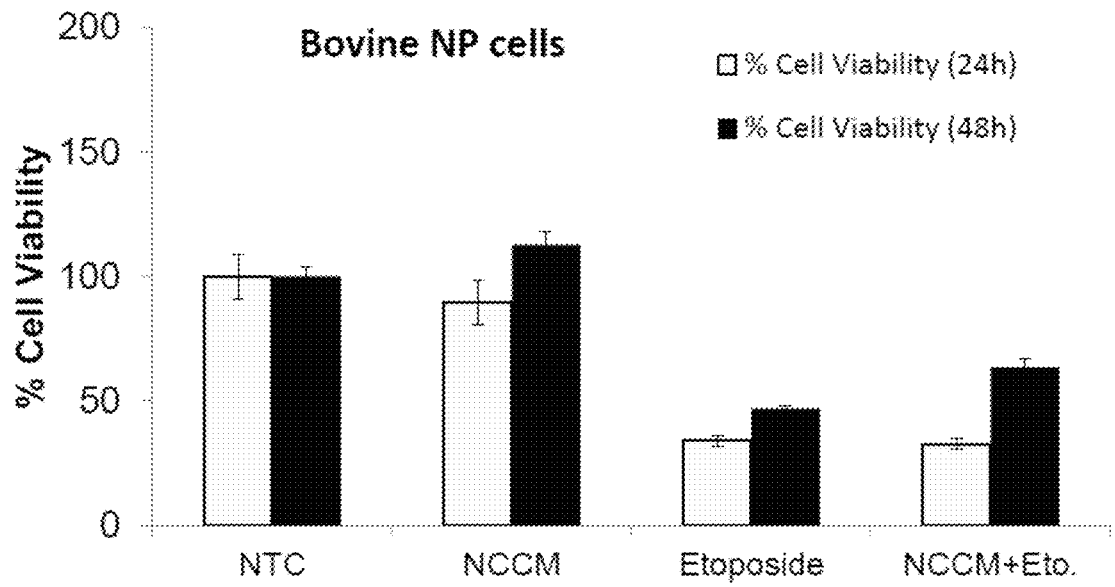
FIGS. 8a-8c shows Evaluation of bioactivity in protein containing fractions (PF) collected after size exclusion chromatography. Histograms showing (FIG. 8a) cell viability, (FIG. 8b) caspase 3/7 activity in bovine NP cells treated with NCCM, the cytotoxic drug, etoposide (300 μM, used as a positive control) in presence of NCCM or control medium (serum, phenol red and protein free Hybridoma Media). Each bar represents mean±S.D. of 2 independent experiments done in triplicates (n=6).
Figure 8B:
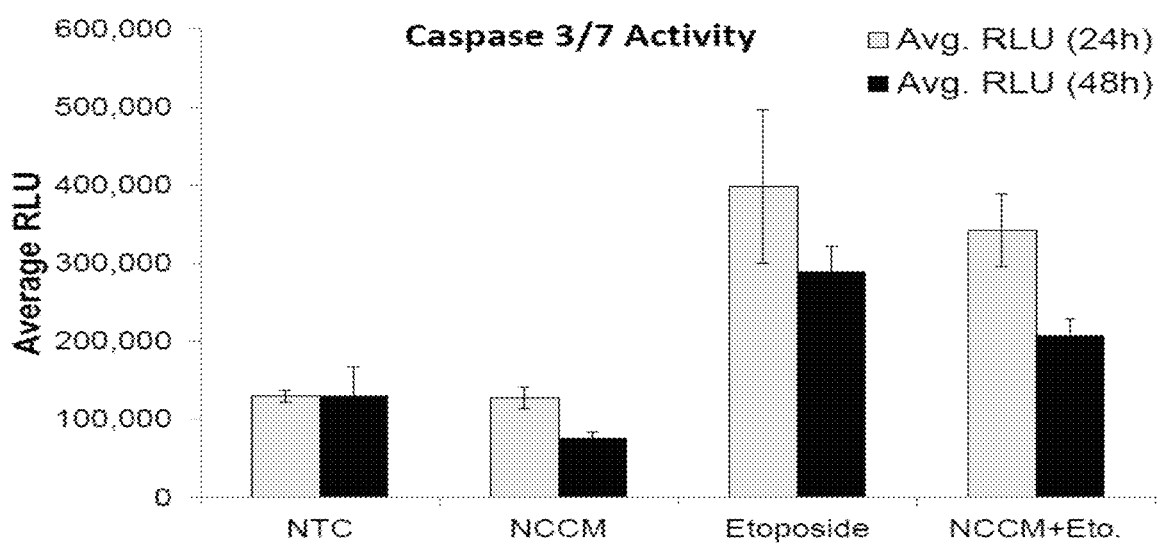
Figure 8C:
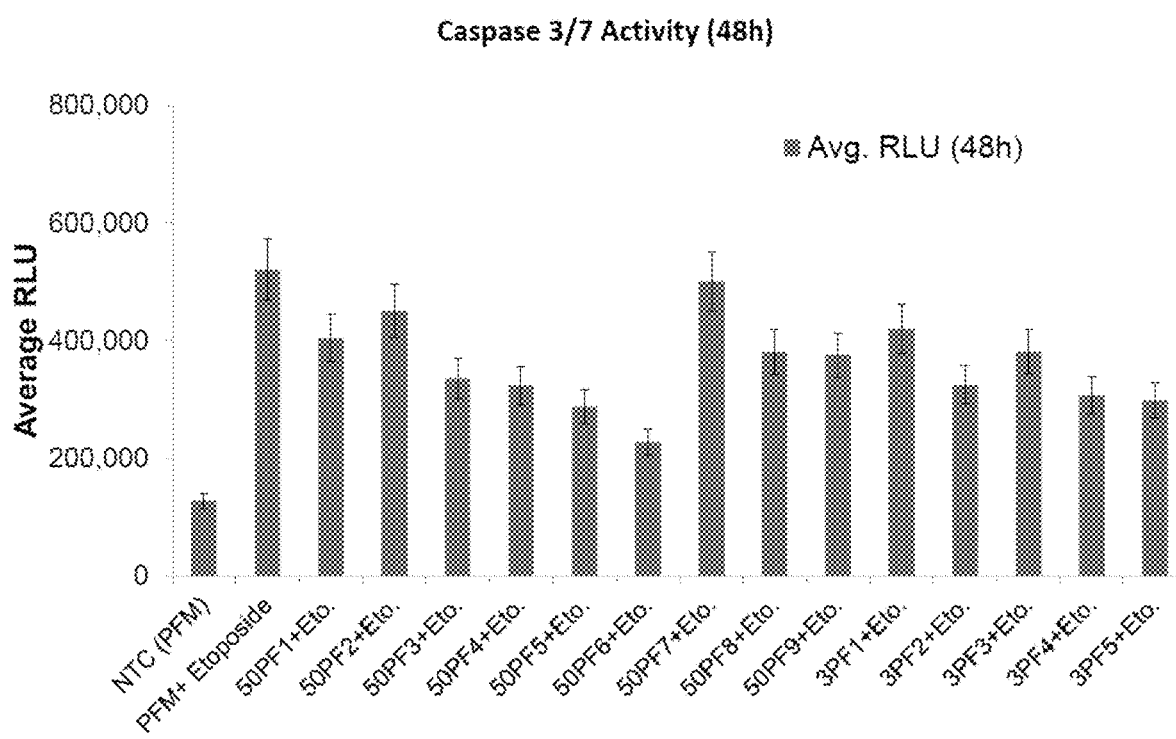

To identify the soluble factors secreted by NCs, NCCM was concentrated sequentially using 50 kDa and 3 kDa filters, followed by fractionation using size exclusion chromatography (FIG. 3c). Among the protein containing fractions, only five fractions (50 PF4, 50 PF5, 50 PF6, 3 PF4 and 3 PF5) reduced etoposide-induced caspase 3/7 activity in bovine NP cells (FIG. 8a-c). Mass spectroscopic analysis of these bioactive fractions led to the identification of 303 non-redundant proteins corresponding to the canine protein database (FIG. 3c).

Figure 9:
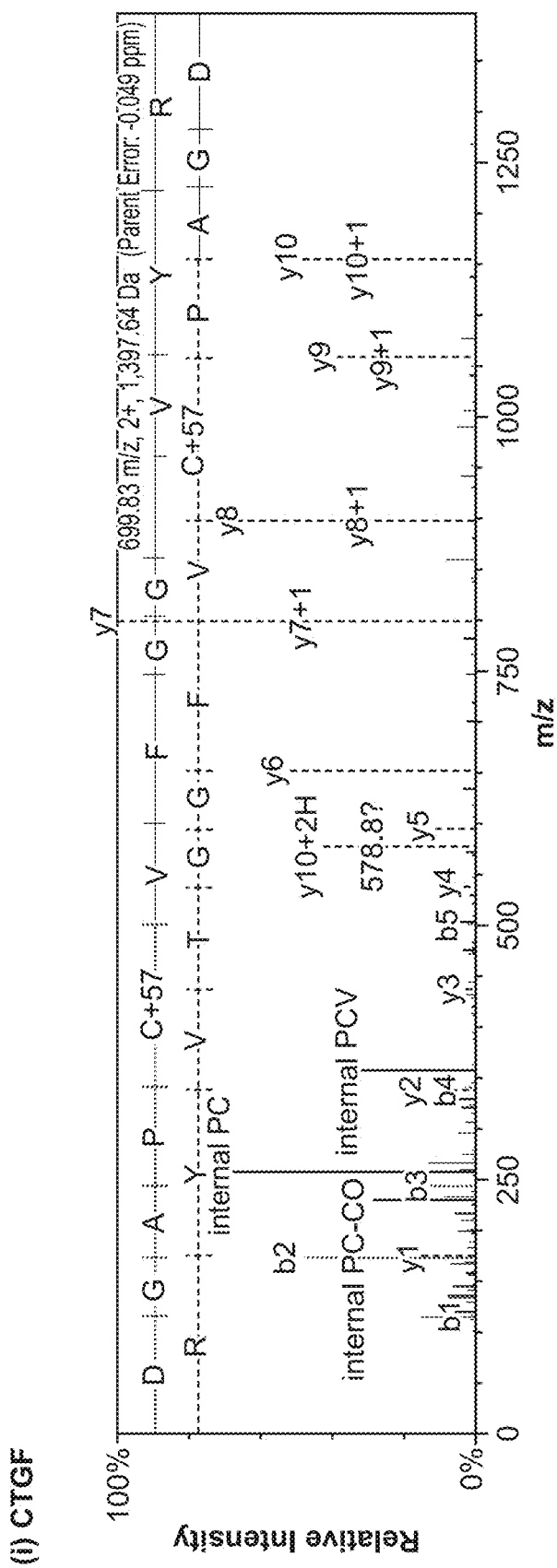
FIG. 9 shows Peptide signature peaks for CTGF, WISP-2 and TGFβ1 observed in mass-spectroscopy analysis of NCCM.
Figure 10A:
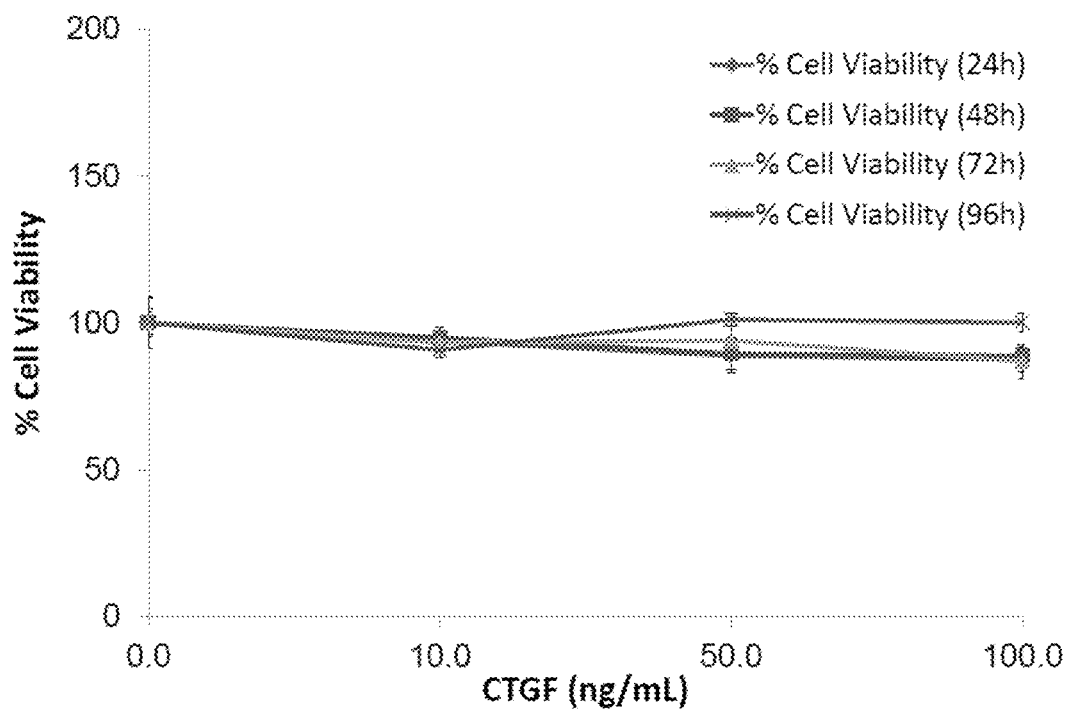
FIGS. 10a-10d shows Dose (1 ng/mL-100 ng/mL) and time dependent (24 hrs-96 hrs) effects of (FIG. 10a) CTGF, (FIG. 10b) WISP-2 and (FIG. 10c) TGFβ1 treatment alone or (FIG. 10d) combination of CTGF with WISP-2, and TGFβ1 on cell viability determined using MTT assays in NP cells obtained from healthy rat IVDs. Each bar represents mean±S.D. of 3 independent experiments done in quadruplicates (n=12).
Figure 10B:
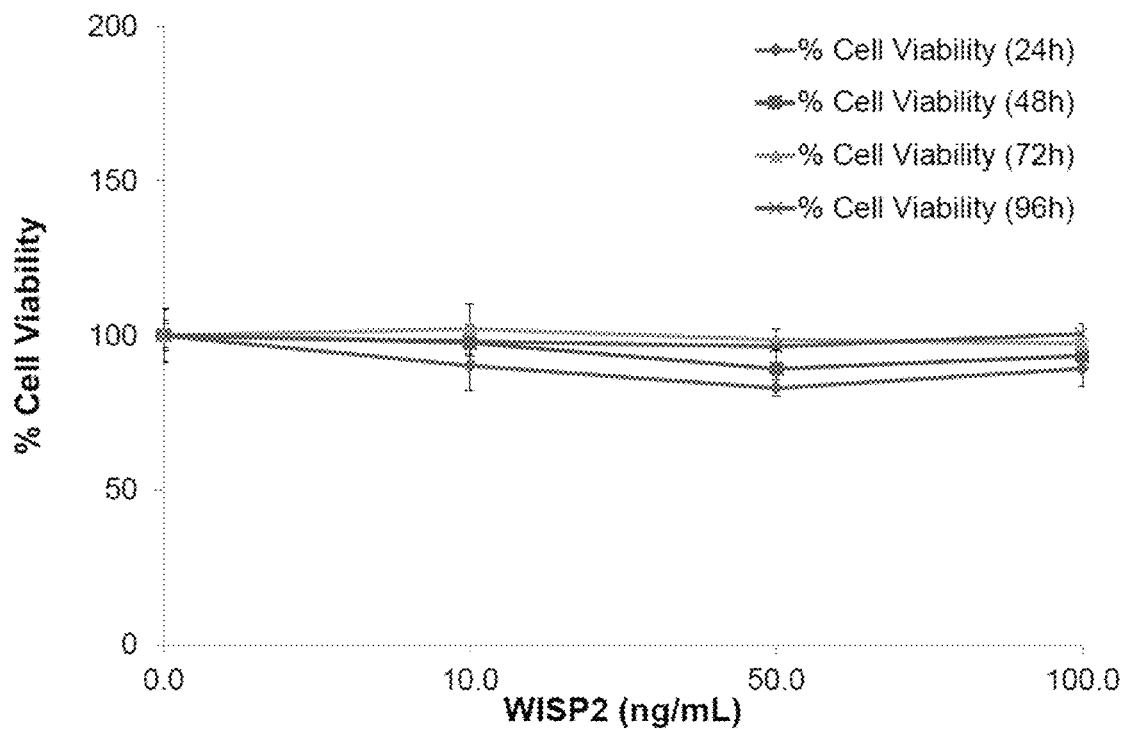
Figure 10C:
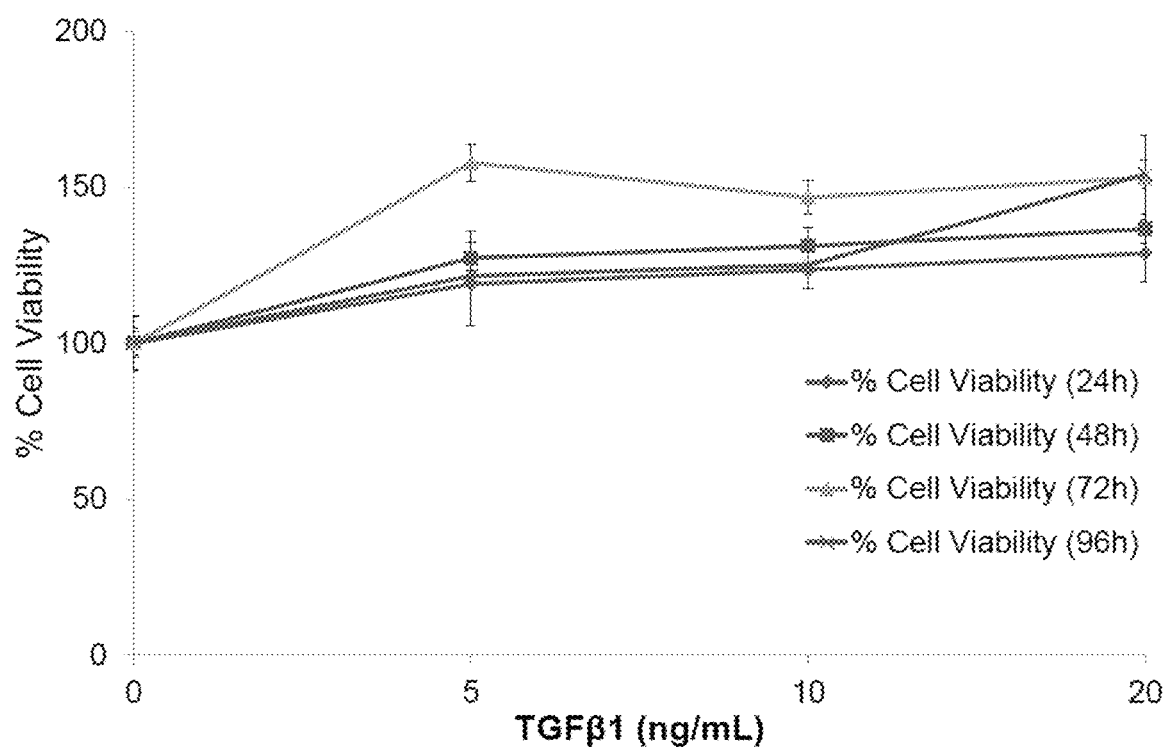
Figure 10D:
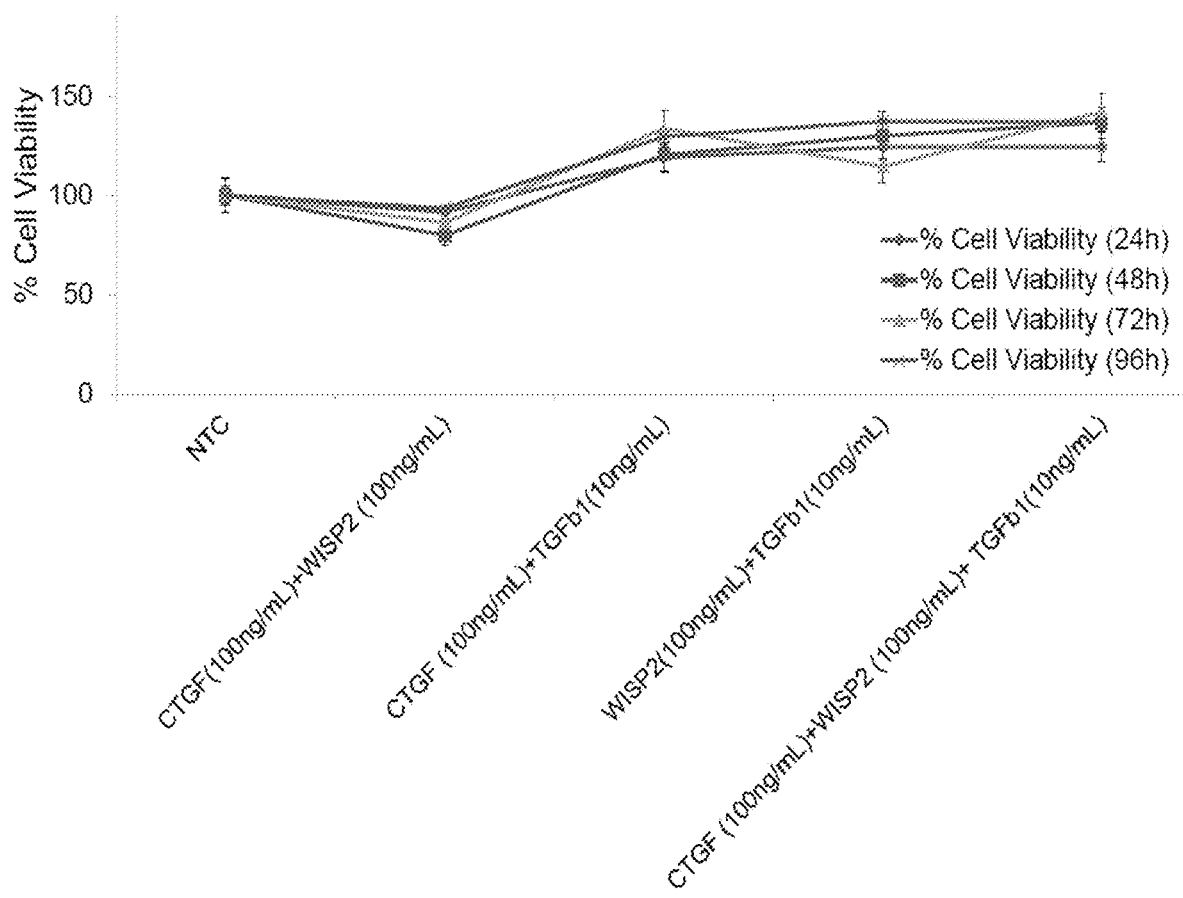

Approximately 31% of these proteins had a secretory peptide signal sequence and have been reported within ECM (FIG. 3d). Growth factors and their modulators were identified including TGFβ1, connective tissue growth factor (CTGF), Wnt-induced soluble protein-2 (WISP-2), chordin, sclerostin, cartilage intermediate layer protein (CILP) and CD109 (FIG. 9). Immunohistochemical analysis demonstrated moderate to strong immunostaining of CTGF, WISP-2 and TGFβ1 in the cytoplasm of NC cells and the ECM in healthy rat-tail disc NPs. However, injured rat-tail disc and human degenerated disc NPs showed no detectable expression of CTGF, WISP-2 or TGFβ1 within the ECM (FIG. 3e). These findings suggested that the loss of CTGF, WISP-2 or TGFβ1 is associated with the development of DDD.

CTGF and TGFβ1 Confers Anabolic and Anti-Catabolic Effects on NP Cells In Vitro

Figure 4A:
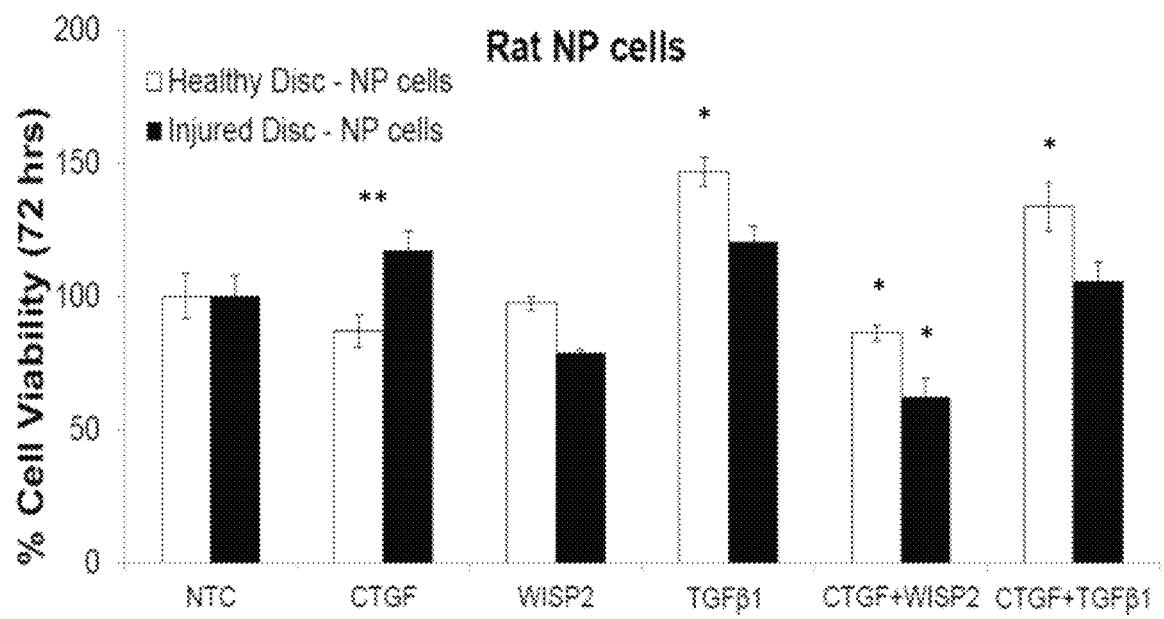
FIGS. 4a-4g shows Anabolic effects of CTGF, WISP-2 and TGFβ1 in an in vitro model of DDD.
Figure 4B:
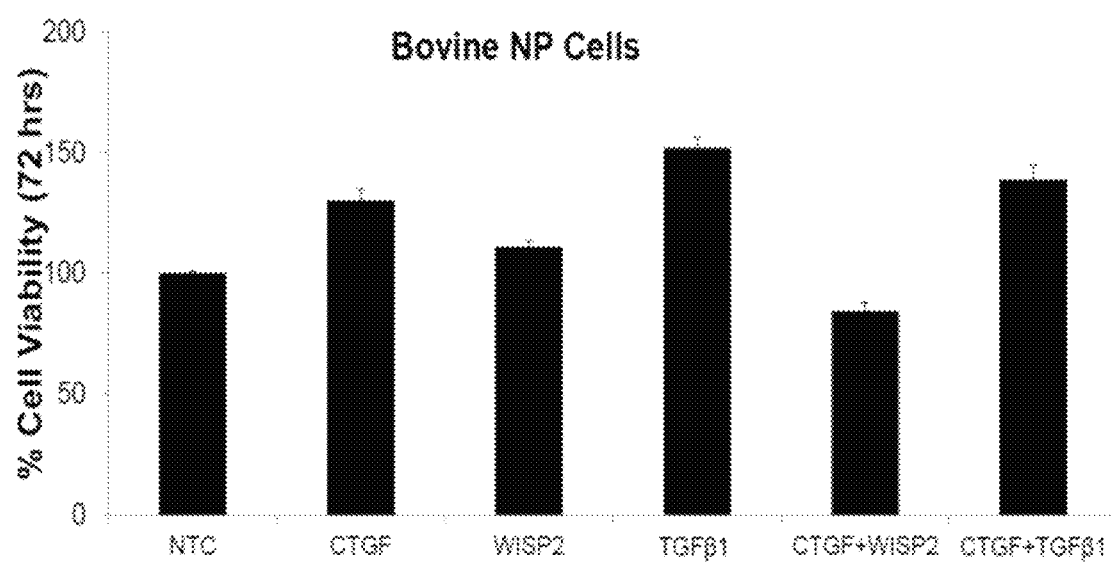
Figure 4C:
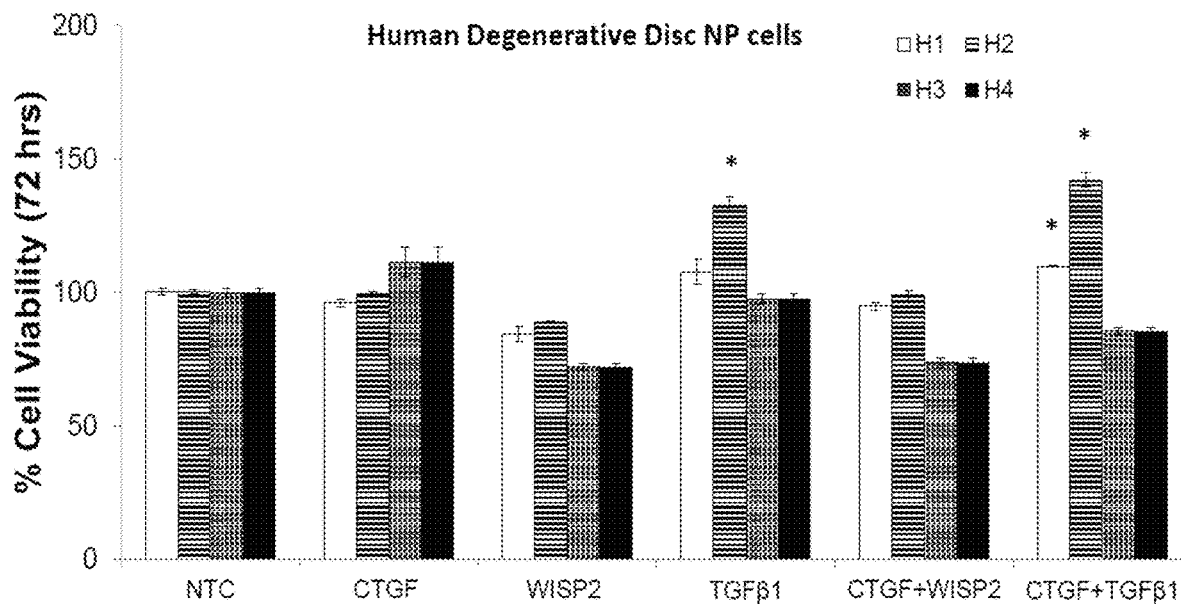
Figure 4D:
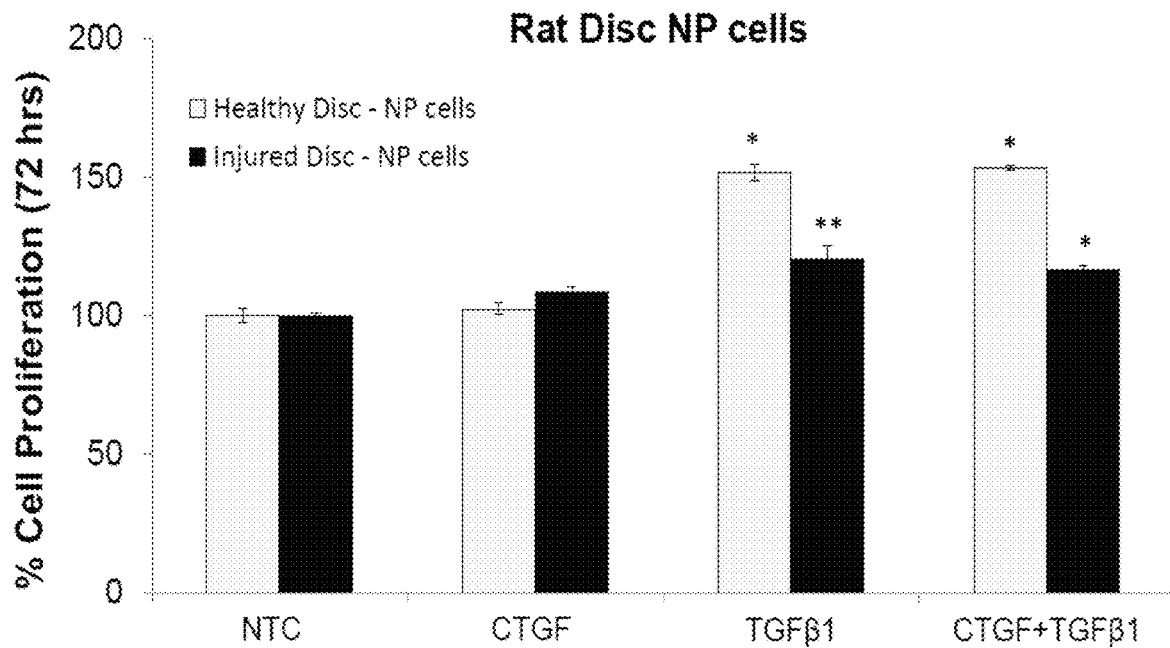
Figure 4E:
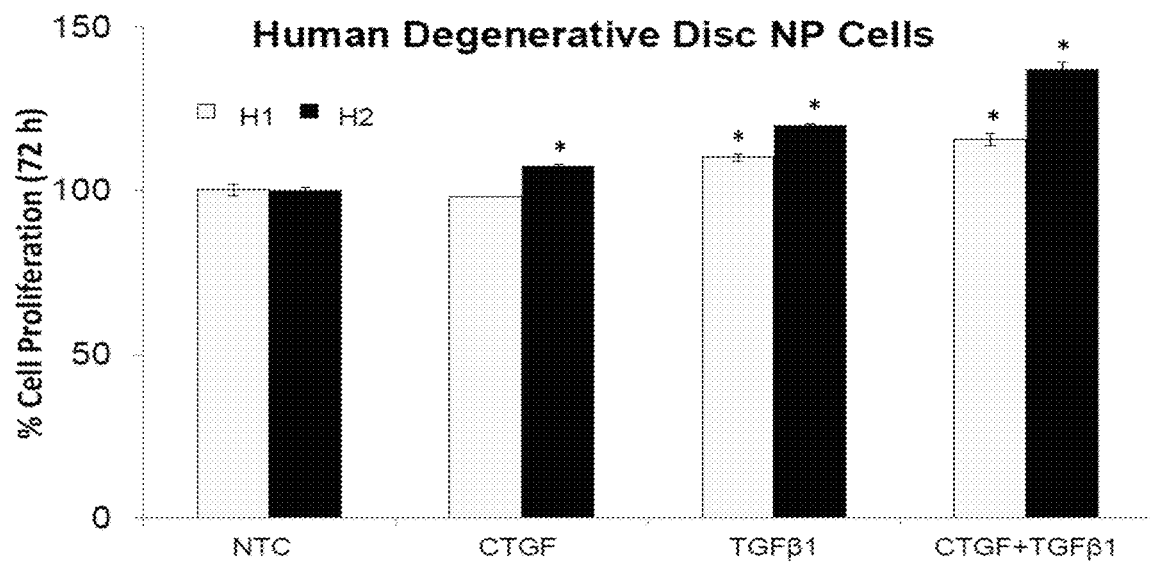
Figure 4F:
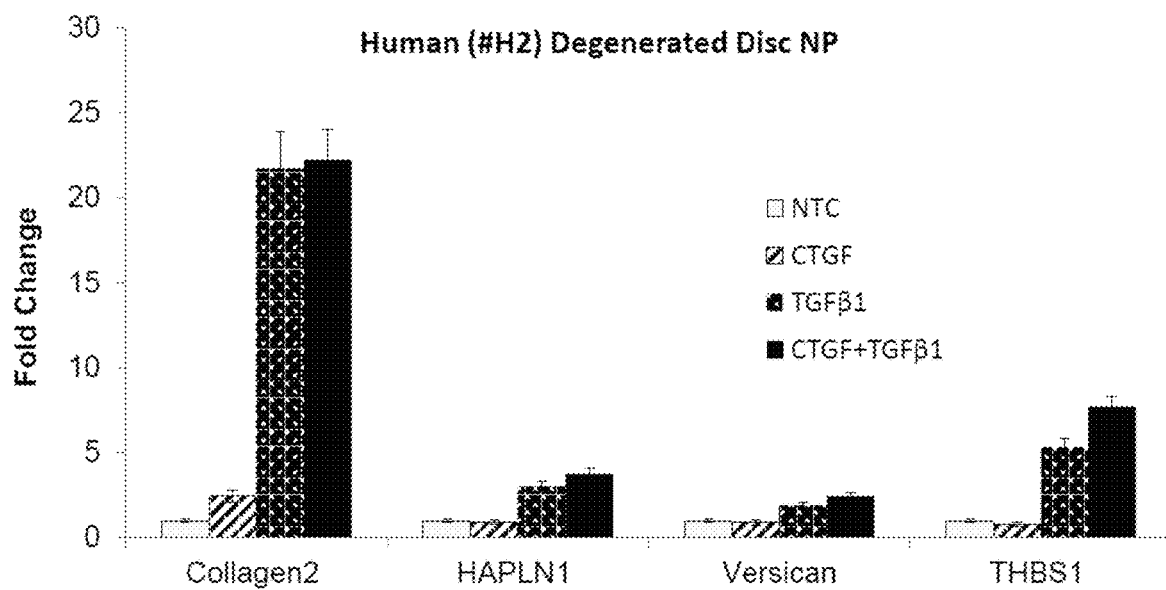
Figure 4G:
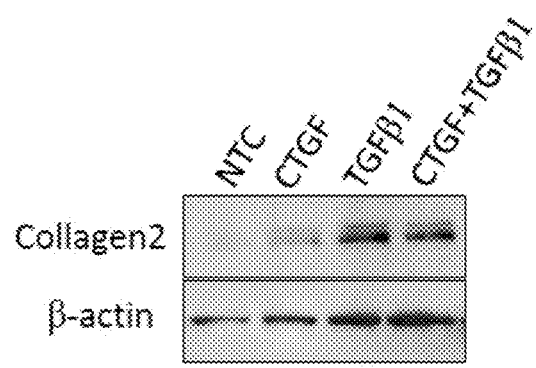
Figure 11:
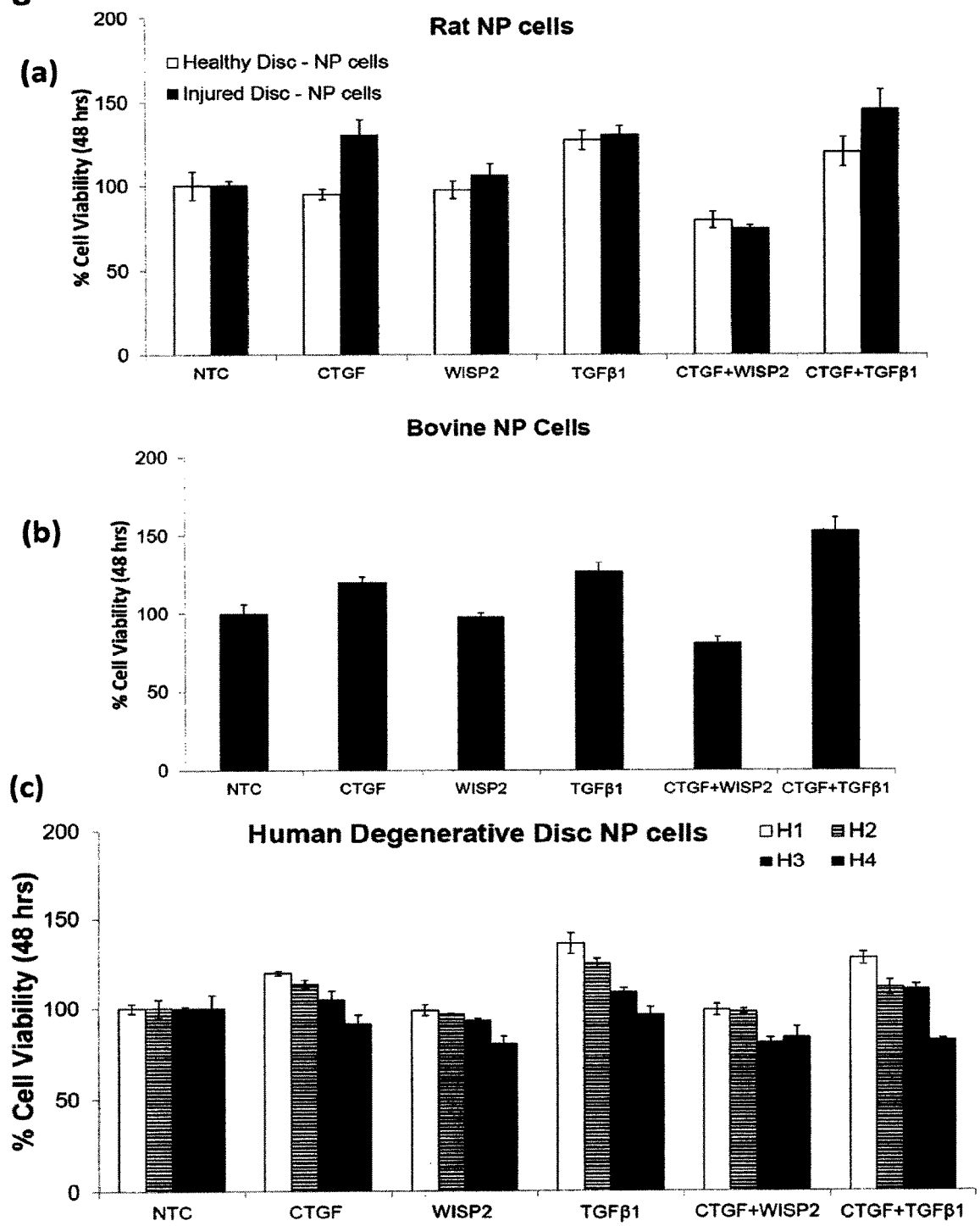
FIGS. 11a-11c shows Effect of CTGF, WISP-2 and TGFβ1 treatment alone or in combination on cell viability as determined using MTT assays in NP cells obtained from (FIG. 11a) rat (healthy/injured) disc, *p<1.02, (FIG. 11b) bovine degenerative disc, *p<0.01 and (FIG. 11c) human (H1-H4) degenerative NP cells in 48 hrs (*p<0.005, **p=0.02). Each bar represents mean±S.D. of 3 independent experiments done in triplicates (n=9).

Rat-tail disc NP cells (healthy/degenerated) were treated with CTGF, WISP-2 or TGFβ1 to evaluate their effect on cell viability in a dose and time dependent manner (24 hrs-96 hrs, FIG. 10a-d). Cell viability was determined using 3-(4,5-dimethylthiazol-2-yl)-2,5-diphenyltetrazolium bromide (MTT) based colorimetric assays. Treatment with CTGF (100 ng/ml) or TGFβ1 (10 ng/ml) alone or in combination increased the viability of NP cells derived from rat-tail discs (healthy/injured) and bovine discs in 48 hrs-72 hrs (FIG. 4a, b, FIG. 11a, b). Notably, treatment with a combination of CTGF (100 ng/ml) and TGFβ1 (10 ng/ml) increased cell viability by ≥35% in human degenerated disc NP cells (FIG. 4c, FIG. 11c). However, no significant change in viability of NP cells (rat and human) was observed on treatment with WISP-2 (FIG. 4a-c, FIG. 10b, 5a-c). This was further confirmed with cell proliferation assays using bromodeoxyuridine (BrdU) incorporation. Significant increase in DNA synthesis was observed in rat-tail (healthy/injured) and human degenerated disc NP cells on treatment with TGFβ1 alone (FIG. 4d, e). Increased mRNA levels of collagen 2, hyaluronan and proteoglycan link protein 1 (HAPLN1), versican and thrombospondin1 (THBS1) were also observed in human degenerated disc NP cells on treatment with a TGFβ1 alone or in combination with CTGF (FIG. 4f). Western blotting verified an increase in collagen 2 expression on treatment with TGFβ1 alone or in combination with CTGF within 24 hrs (FIG. 4g), supporting the anabolic roles of these growth factors.

Figure 5A:
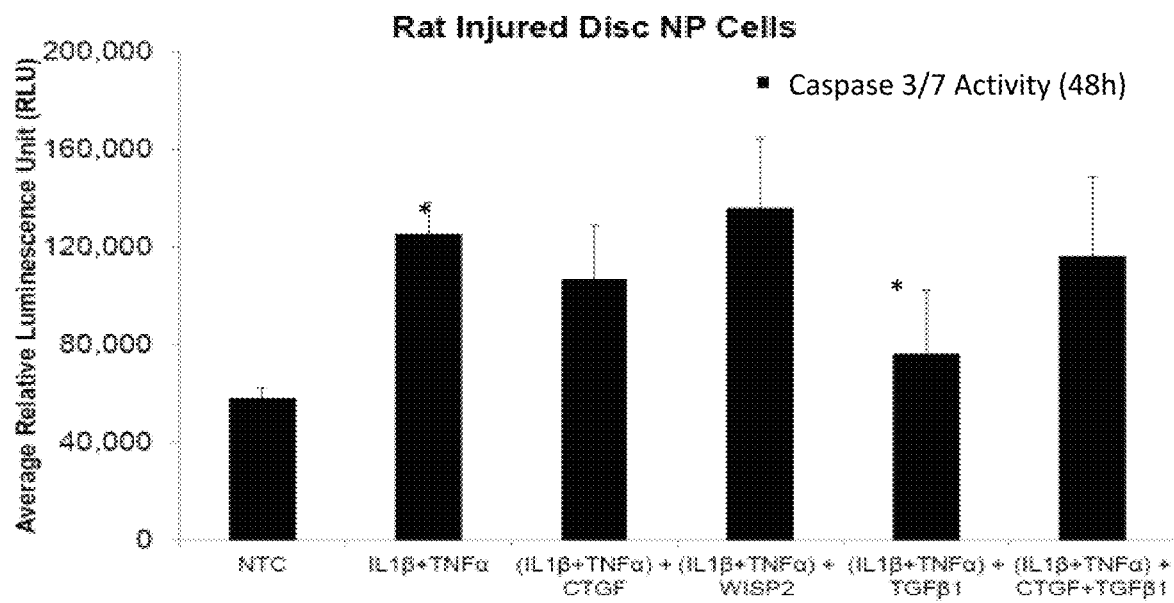
FIGS. 5a-5j shows Anti-catabolic effects of CTGF, WISP-2 and TGFβ1 in an in vitro model of DDD. (a) Histograms showing caspase 3/7 activity in NP cells derived from (FIG. 5a) rat injured IVD (*p=0.008, **p=0.05), (FIG. 5b, FIG. 5c) human degenerative disc NP treated with pro-inflammatory cytokines, IL-1β and TNFα alone or in presence of CTGF, WISP-2 and TGFβ1(*p<0.05). Histograms showing caspase 9 activity in NP cells (FIG. 5d) rat injured IVD, (FIG. 5e, FIG. 5f) human degenerative disc NP treated with pro-inflammatory cytokines, IL-1β and TNFα alone or in presence of CTGF, WISP-2 and TGFβ1(*p<0.05, **p<0.005). Each bar in the caspase assays is showing mean±S.D. of 2 independent experiments done in quadruplets (n=8). The p-values were determined using paired Student's t-test. For the combination of IL-1β and TNFα are with respect to no treatment control (NTC), while p-values for the groups containing growth factors (CTGF, WISP-2 or TGFβ1) are with respect to the group containing combination of IL-1β and TNFα only. Western blot analysis of MMP-3, MMP-13 and Cox2 in rat healthy IVD NP cells treated with (FIG. 5g) IL-1β alone, (FIG. 5h) IL-1β and TNFα in combination, and in the presence of CTGF, WISP-2 or TGFβ1. Histograms showing decreased expression of (FIG. 5i) Cox2, (FIG. 5j) MMP-13 mRNA levels in human degenerative disc NP cells treated with IL-1β and TNFα in presence of CTGF and TGFβ1 in comparison to IL-1β and TNFα only treatments. Each bar in the histogram represents mean±S.D. of 3 independent experiments done in duplicates (n=6,*p<0.001).
Figure 5B:
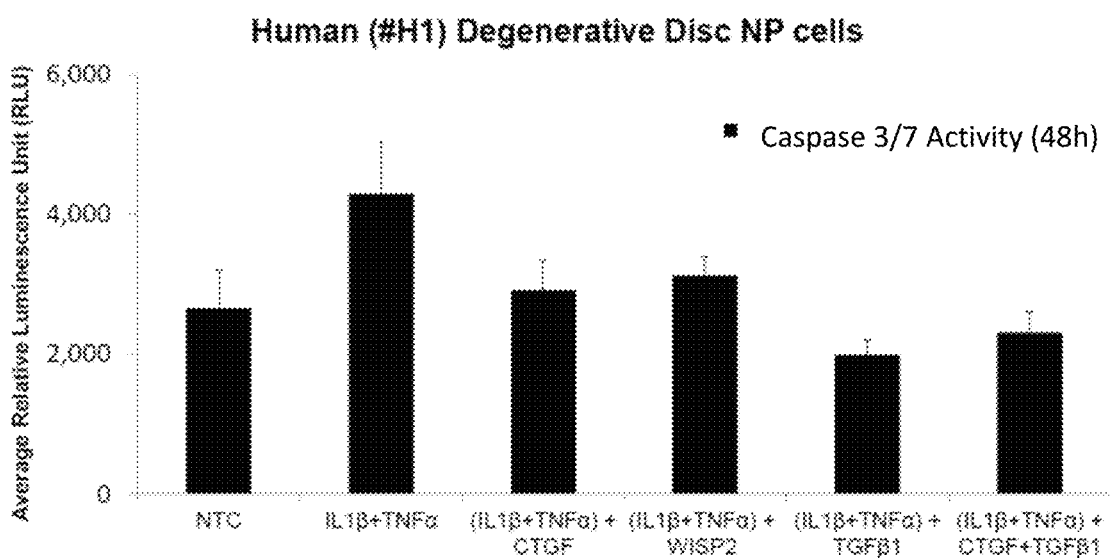
Figure 5C:
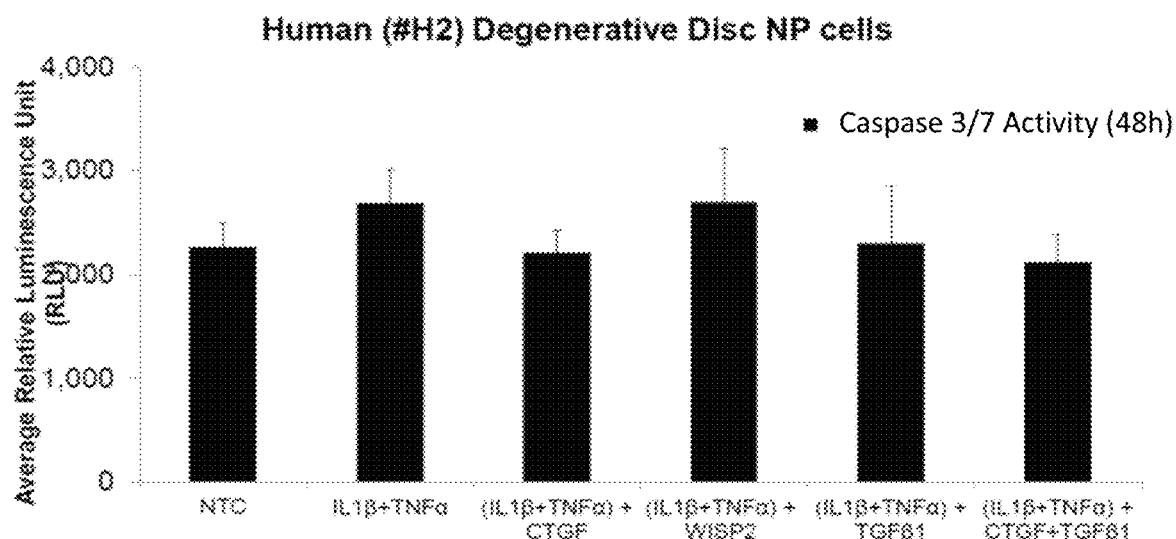
Figure 5D:
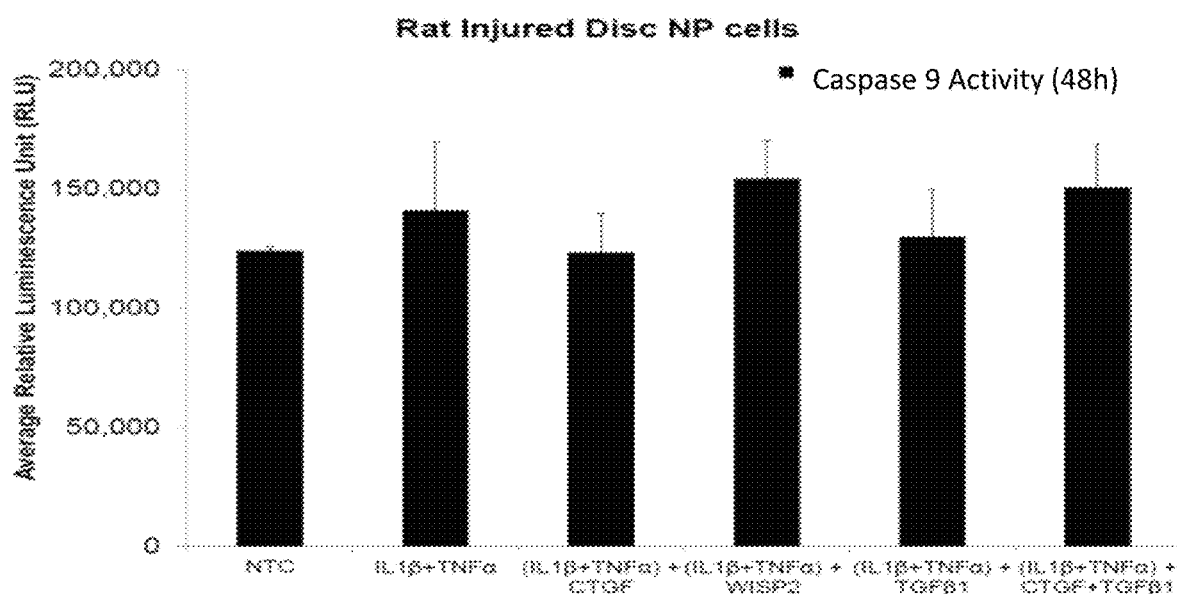
Figure 5E:
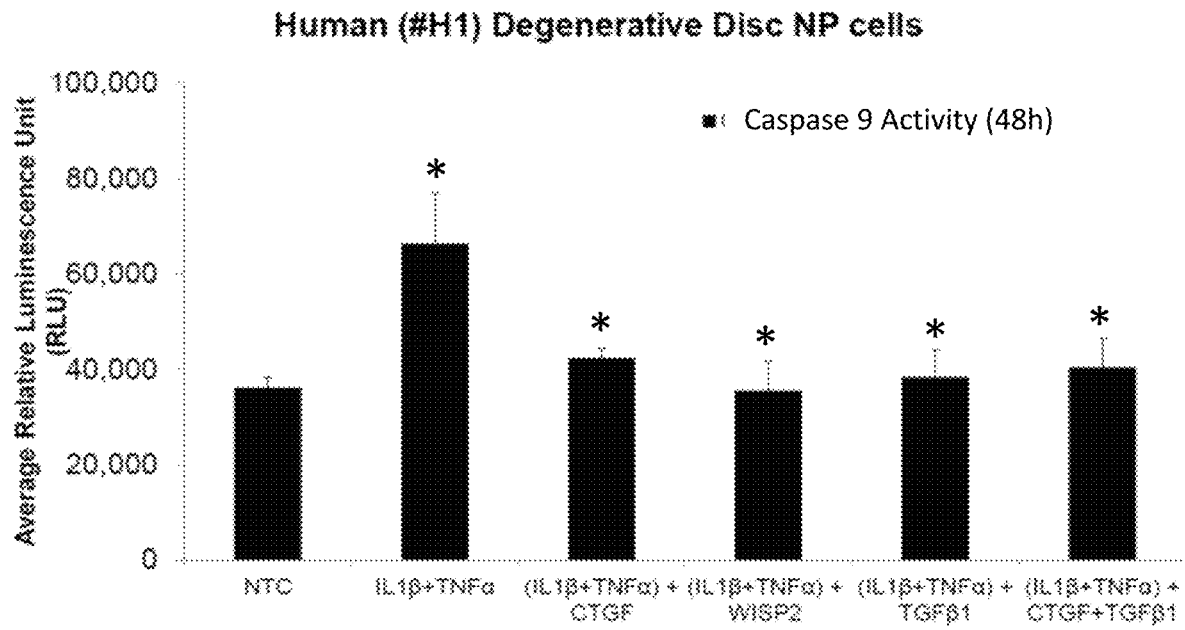
Figure 5F:
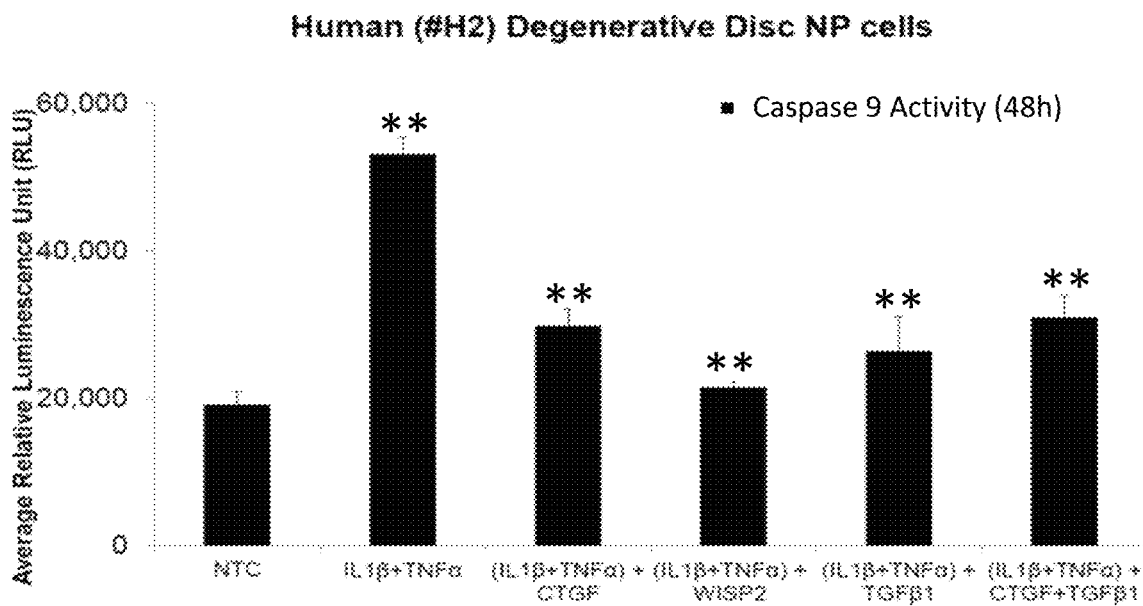
Figure 5G:
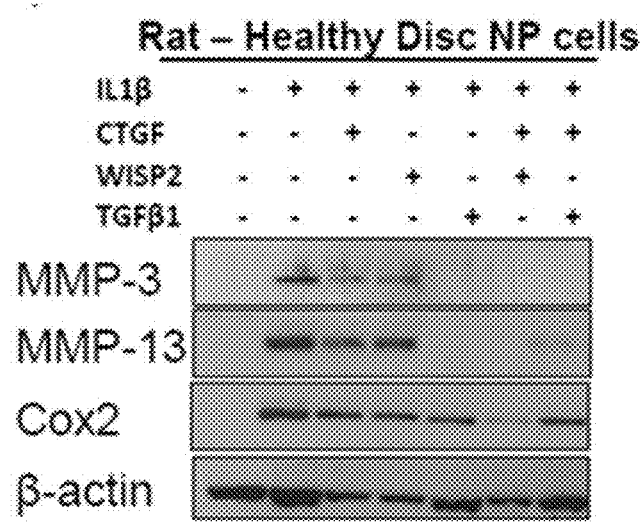
Figure 5H:
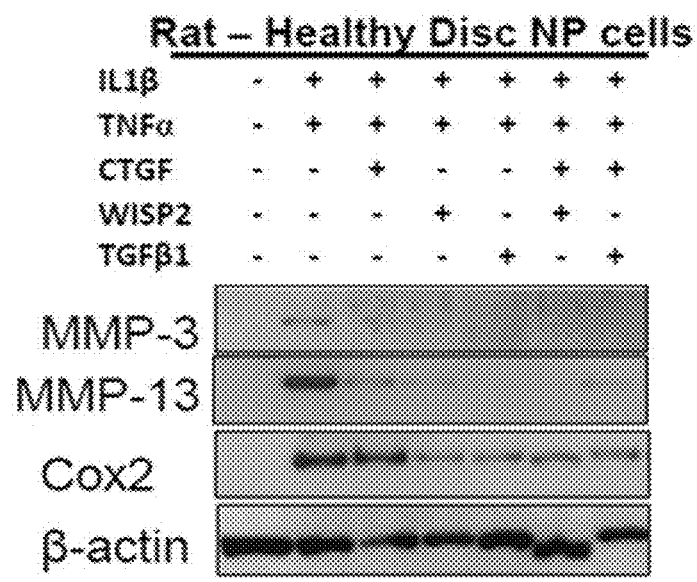
Figure 5I:
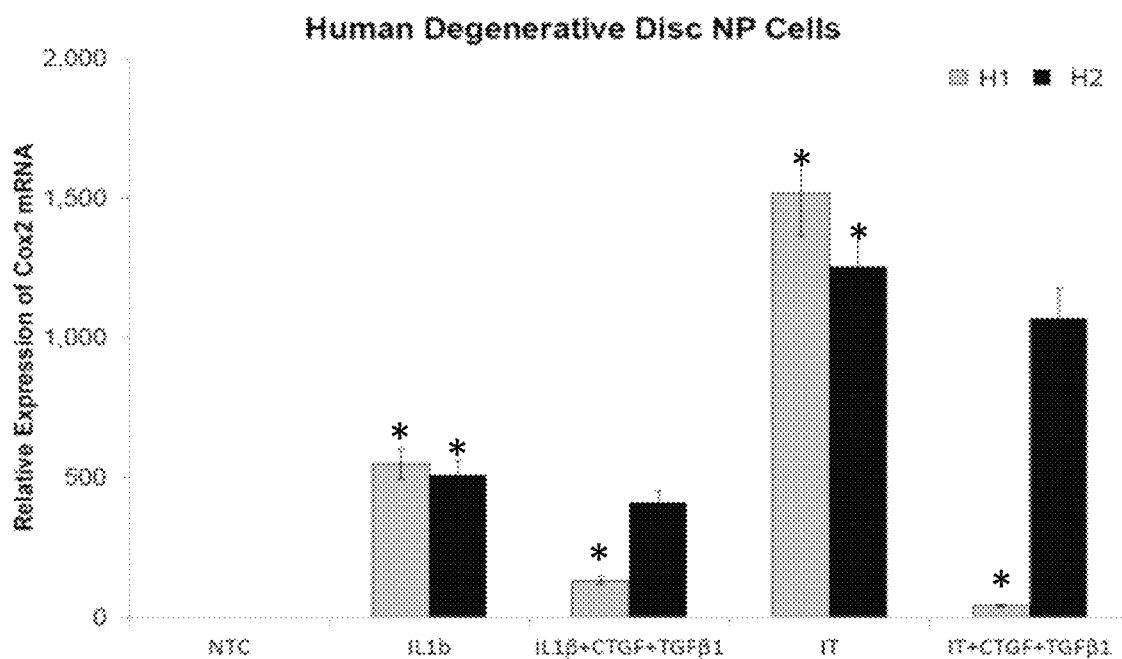
Figure 5J:
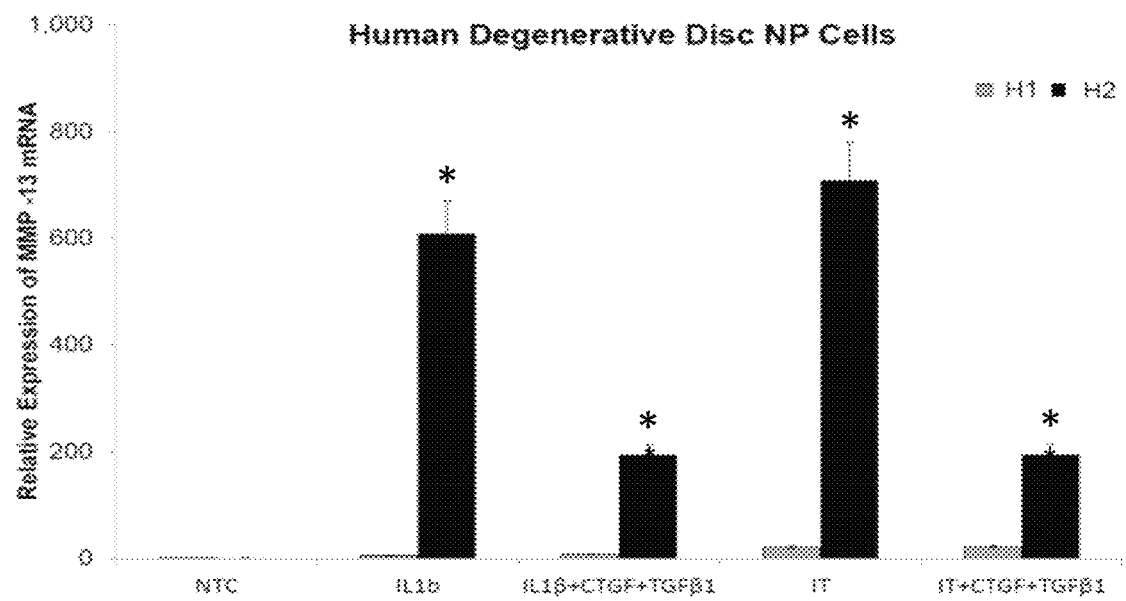

The potential of CTGF and TGFβ1 to suppress inflammation induced caspase activity and the expression of MMPs was evaluated. Both rat and human degenerative disc NP cells were treated with IL-1β alone or in combination with TNFα in the presence of CTGF, WISP-2 or TGFβ1 for 48 hrs. Results revealed a significant decrease in cytokine (IL-1β and TNFα)-induced caspase 3/7 activity in degenerative disc NP cells (rat/human) in the presence of TGFβ1 alone (FIG. 5a-c). In contrast, a significant reduction in IL-1β and TNFα induced caspase 9 activity was observed in the presence of either CTGF, WISP-2 or TGFβ1 in human degenerative disc NP cells (FIG. 5e,f). Treatment with CTGF, WISP-2 or TGFβ1 reduced expression of MMP-3, MMP-13 and Cox2 proteins in rat-tail NP cells treated with IL-1β and TNFα (FIG. 5g, h). Similarly, human degenerative disc NP cells treated with IL-1β and TNFα showed lower levels of Cox2 and MMP-13 mRNA levels in presence of a combination of CTGF and TGFβ1 demonstrating the anti-catabolic effect of these growth factors (FIG. 5i,j).

Treatment with CTGF and TGFβ1 Regenerates the Degenerative Disc Nucleus Pulposus In Vivo Results thus far suggested the anti-catabolic and pro-anabolic roles of CTGF and TGFβ1 in in vitro. To test the regenerative potential of CTGF and TGFβ1 in a rodent model, image guided tail disc injury (n=30, 4 discs/animal) was performed in 2 independent experiments. Four weeks following injury, animals were randomized into 5 groups (n=6 animals/group) and an intra-discal injection of CTGF (100 ng/mL), TGFβ1 (10 ng/mL), a combination of CTGF (100 ng/mL) and TGFβ1 (10 ng/mL) or phosphate buffered saline (PBS, 1×, pH=7.2) as a vehicle control was given. Histological analysis of discs injected with PBS (1×, pH=7.2) showed few cells with a fibrocartilaginous matrix and intense Safranin-O staining within the NP (FIG. 6a). However, injured rat-tail discs treated with CTGF or TGFβ1 alone or in combination, demonstrated a healthy disc, rich in NCs, 10 weeks post-injury (FIG. 6a). Immunohistochemical analysis confirmed the restoration of a healthy NP, showing strong expression of aggrecan and collagen II, as compared to injured disc NPs injected with vehicle control (FIG. 6a, b). Treatment with the combination of CTGF and TGFβ1 suppressed MMP-13 and Cox2 proteins, and restored expression of Brachyury and Oct4 in rat-tail injured disc NPs (FIG. 6b).

DDD is a multifactorial process characterized by the loss of IVD structural integrity, and the development of an inferior NP ECM often leading to a painful disc and limited mobility[27-31]. In healthy IVD NPs, the hydrophilic ECM plays an important role in maintaining the biomechanical properties of the spine. The Examples show that deterioration of the NP-ECM in a rodent model of DDD is associated with inflammation, and the loss of notochordal and stem cells, which collectively lead to the development of a fibrocartilaginous NP, similar to that observed in human degenerative discs. These findings demonstrate a direct relationship between expression of pro-inflammatory cytokines (TNFα and IL-1β) and matrix degrading enzymes (MMP-3, MMP-13, ADAMTS4) in DDD. Treatment with these pro-inflammatory cytokines in vitro established a significant role for inflammation in the regulation of ECM degradation and turnover, during progressive disc degeneration. Therefore, targeting inflammation in a degenerative disc NP may be the key for treatment of DDD. Several single agent strategies have been designed and tested targeting inflammation in DDD, including an interleukin 1 receptor antagonist (IL-1 Ra), as well as synthetic peptides and inhibitors targeting TNFα and its major downstream target, NFκB[32-39]. In support, it was also shown that inhibition of NFκB or MAPK (p42/44 and p38MAPK), Jak1 and STAT3 are capable of reducing Cox2, MMP-3 and MMP-13 expression downstream of IL-1β and TNFα in NP cells. However, the action of these specific inhibitors as therapeutic agents is limited to anti-catabolic activity. These agents fail to show any anabolic response that catalyzes de novo synthesis of healthy NP ECM or promote NP cell viability and proliferation in a degenerating IVD.

The present inventors identified TGFβ1, CTGF and WISP-2 in NCCM and demonstrated their regenerative potential. TGFβ1 plays a critical role in the development of the IVD and cartilage in the embryonic stage as well as post-natal development of the spine[40]. Loss of TGFβ signaling in end plate chondrocytes and inner annulus fibrosus cells leads to the loss of matrix tissue, and abnormal growth plate morphology in the spines of TGFβ1-null mice[40]. The data also showed reduced TGFβ1 expression in degenerated, fibrocartilaginous NP in both human and injured rat-tail discs. The loss of TGFβ1 in degenerative disc NPs indicates the importance of TGFβ signaling for the maintenance of a healthy, NC rich nucleus pulposus. TGFβ1 overexpression in healthy rabbit NPs showed a significant increase in proteoglycan synthesis in comparison to IVDs injected with control adenoviral vectors or saline.

Another therapeutic agent, CTGF identified in NCCM is a matricellular protein that possesses an amino-terminal secretory peptide followed by four conserved domains with sequence homologies to insulin-like growth factor-binding proteins, von Willebrand factor C (VWC) domain, thrombospondin type 1 repeat (TSR) and a carboxy-terminal domain that contains a cysteine-knot motif. CTGF is an important constituent of the intervertebral disc microenvironment and interacts with several growth factors and matrix proteins including integrins and heparan sulfate proteoglycans. As shown in the Examples, treatment with the combination CTGF and TGFβ1 significantly reduced IL-1β induced expression of Cox2 and matrix degrading enzymes (MMP-3 and MMP-13), both in the in vitro and in vivo models of DDD, indicative of a combined action of these potential therapeutic agents (FIG. 6c).

Figure 12:
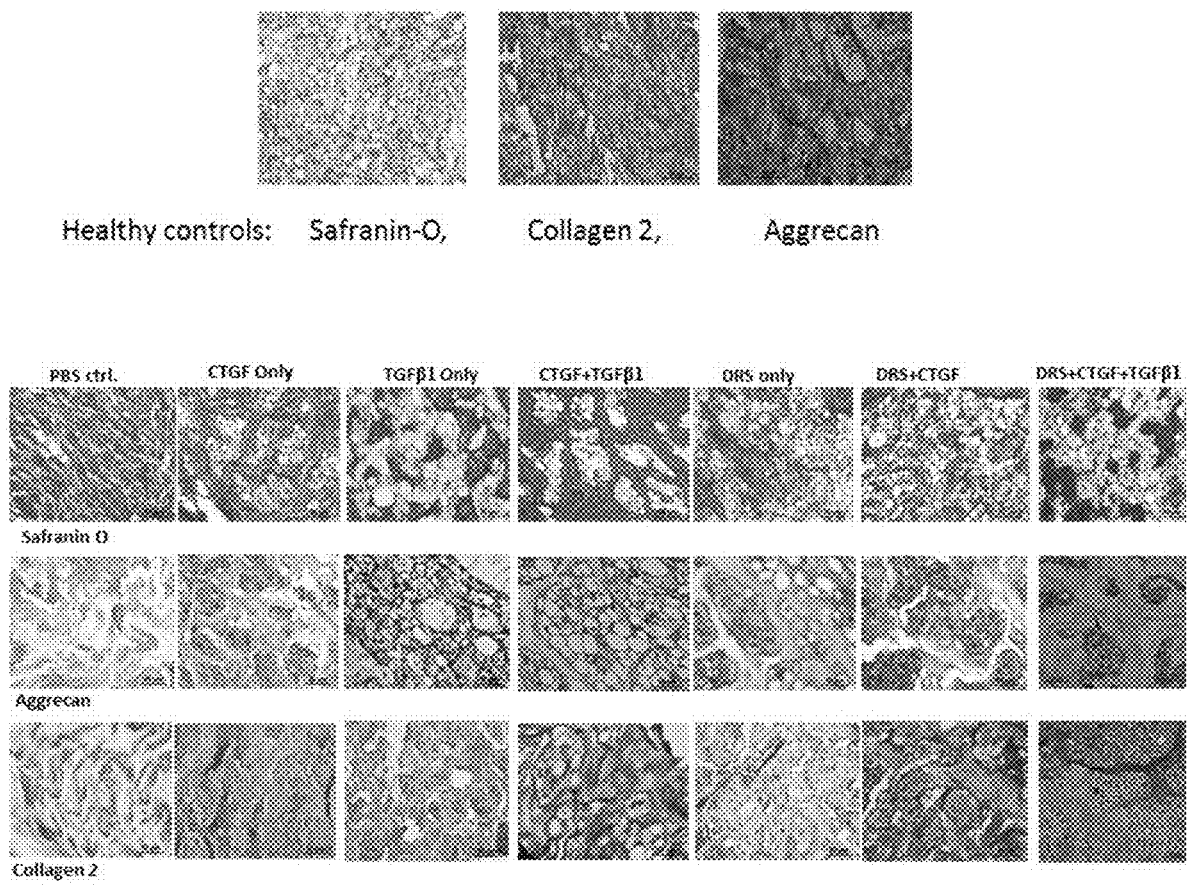
FIGS. 12a-12b show an evaluation of the regenerative potential of CTGF and TGFβ1 alone and in combination with DRS (solution comprising glucosamine hydrochloride and chondroitin sulphate) in a pre-clinical in vivo rodent disc injury model of DDD, showing (FIG. 12a) Safranin-O and immunohistochemical staining of ECM proteins, aggrecan and collagen 2 in paraffin embedded sections of rat tail injured IVD-NPs with phosphate-buffered saline (PBS, used as a control) (Scale bar 50μ).
Figure 12:
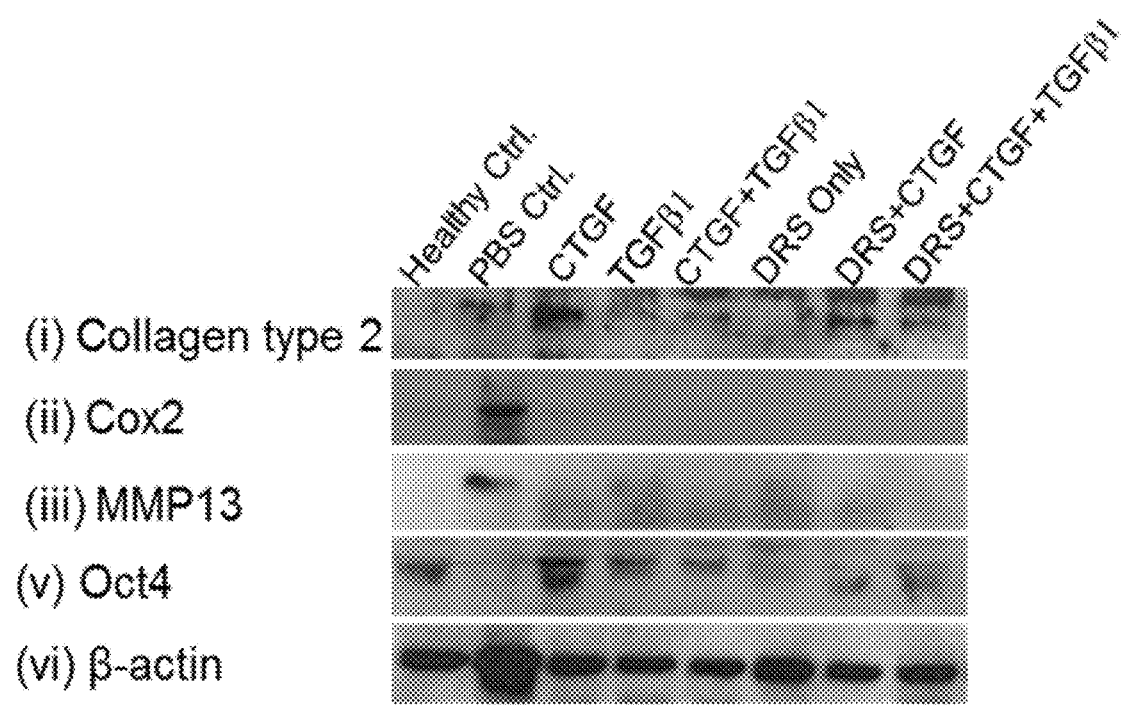

Regenerative Potential of CTGF and TGFβ Alone and in Combination with DRS Composition FIG. 12(a) shows an evaluation of the regenerative potential of CTGF and TGFβ1 alone and in combination with DRS (a composition comprising glucosamine hydrochloride and chondroitin sulphate, prepared as under METHODS) in a in vivo rodent disc injury model of DDD described above. The figure shows Safranin-O and immunohistochemical staining of ECM proteins, aggrecan and collagen 2 with phosphate-buffered saline (PBS, used as a control). This evaluation demonstrated that the DRS+CTGF+TGFβ1 is a particularly effective treatment based on a comparison to healthy controls. FIG. 12(b) provides western blots showing decreased expression of MMP-13 and Cox2, and restoration of the stem cell marker, Oct4 in NP tissue lysates obtained from rat tail injured discs treated with CTGF, TGFβ1, a combination of CTGF and TGFβ1, DRS, DRS in combination with CTGF or a combination of DRS, CTGF and TGFβ1.

Figure 13:
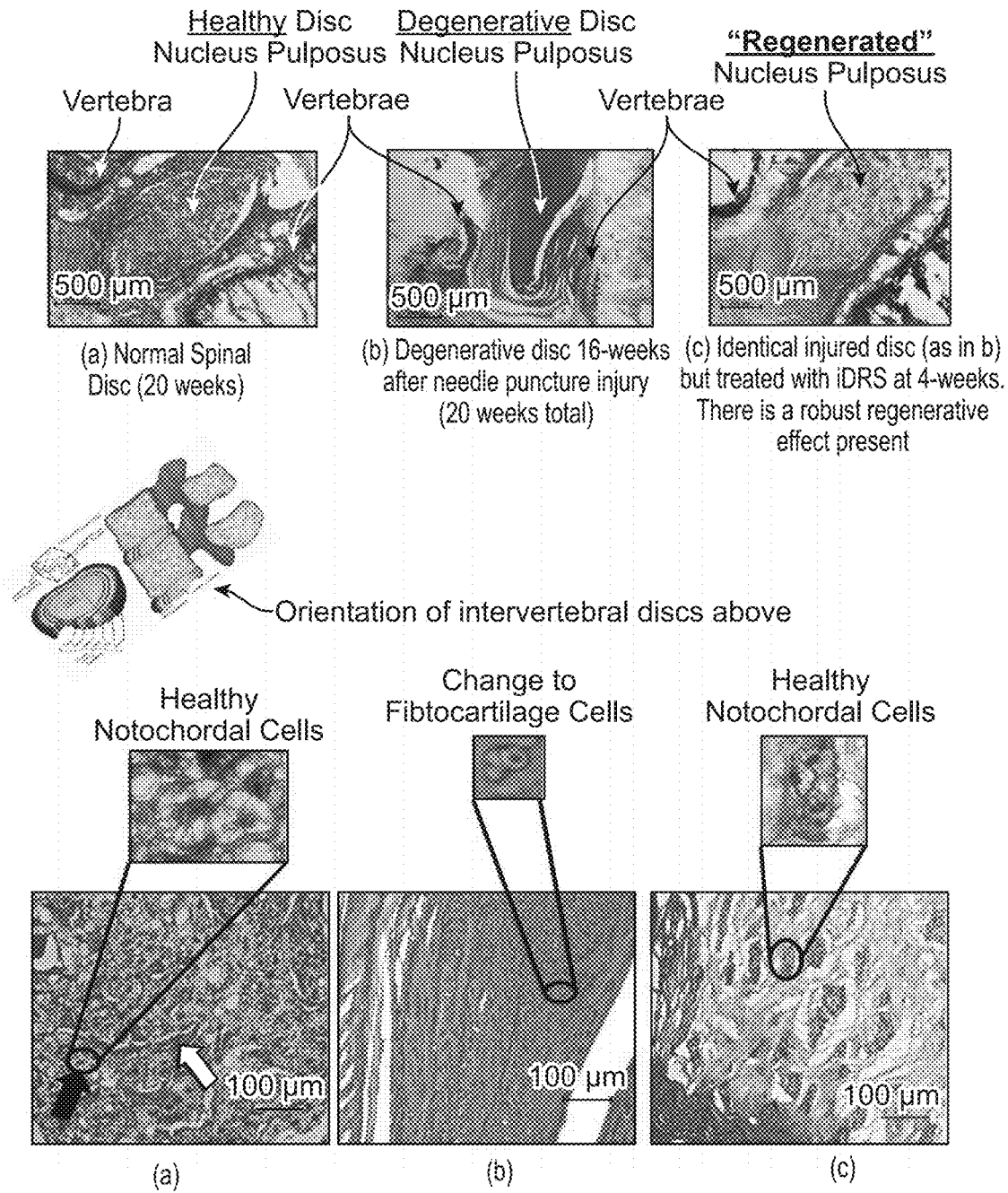
FIG. 13 shows the effects of TGFβ1+CTGF+DRS compared to PBS injections 20-weeks post injury in a rat tail disc injury model. The PBS injected disc demonstrates fibrocartilaginous degenerative changes inclusive of fraying/tearing of the annulus fibrosus, loss of disc height and a degenerative change of the NP cell type. The TGFβ1+CTGF+DRS—injected disc (c) demonstrates a near normal appearing phenotype with preservation of a rich extracellular matrix, notochordal-appearing cells, sustained disc height and healthy annulus fibrosus.

FIG. 13 shows further evaluation through 20 weeks in a rat-tail injury model of DDD: There are three different conditions present. (a) is a Safranin-O stained sagittal section of the rat-tail inter-vertebral disc (IVD) depicting a healthy nucleus pulposus, annulus fibrosus and vertebral end plates (red arrows). (b) Saf-O stained degenerative disc induced by needle puncture injury. The disc was injured as per normal methods followed 4-weeks later by an injection of PBS buffered saline and harvested 16 weeks post injection (20 weeks post injury). Results for the injury control are demonstrative of a profoundly degenerative phenotype with a distinct loss of height, tissue morphology, loss of notochordal cells and the development of a fibrocartilagenous extracellular matrix. (c) Identical experiment except 4-weeks post injury, a composition comprising CTGF, TGFβ1, and DRS was injected rather than saline. This treated disc reveals a near normal phenotype and morphology with maintenance of disc height, healthy vertebral endplates and sustained cellularity and healthy extracellular matrix.

METHODS

Notochordal cell derived conditioned medium (NCCM) was collected from notcohordal cell-rich nucleus pulposus (NP) obtained from IVDs of non-chondrodystrophic canines as described earlier[18]. All animals (n=12) were obtained in collaboration with a licensed animal facility and all practices were in accordance with the animal care policies and ethics approval board of Toronto Western Hospital, Toronto, Ontario, Canada. All non-chondrodystrophic canines were 8 to 14 months of age and had failed at adoption or were to be euthanized for other purposes. Deep sedation was achieved using a combination of Acepromazine (10 mg/mL, Atravet-Aerst Pharmaceuticals St. Laurent, Quebec, Canada) mixed with Xylazine 100 mg/mL (Xylomax-Bimeda-NHC Animal Health, Broomhill Road, Tallaght, Dublin, Ireland) at a combined dose of 1 mL/15 Kg body weight. Once deep sedation had occurred, euthanasia was accomplished using intravenous sodium pentobarbital (CDMV) (St. Hyacinthe, Quebec, Canada) at a dose of 30 mL/kg body weight. Within 2 hrs of euthanization, the lumbar spines were removed and nucleus pulposus were isolated under aseptic conditions[18]. Nuclei pulposi were washed with phosphate buffered saline (PBS, pH=7.2) and 2-3 NPs were placed within tissue culture inserts with 10μ-filters in CD Hybridoma media (protein and phenol red free, Cat No #11279-023, Life Technologies, USA) containing 100 units penicillin/streptomycin in 6 well plates under hypoxic conditions (3.5% $O_2$, and 5% $CO_2$, NuAire incubators) at 37° C. The conditioned medium referred hereafter as NCCM was collected after 24 hrs-48 hrs, centrifuged at 8000 rpm for 30 minutes, filtered through 0.2p syringe-tip filters and stored in −80° C. until further use.

NCCM was thawed at room-temperature (RT) and concentrated sequentially using 50 kDa and 3 kDa spin-ultrafiltration protein concentrators (EMD Millipore, Mass., USA) following manufacturer's instructions. The respective concentrated NCCM samples were fractionated by size-exclusion on a Superose 12 HR 10/30 fast protein liquid chromatography (FPLC) column (Pharmacia) in running buffer containing 10 mM sodium phosphate, 150 mM NaCl, 1 mM EDTA, pH 7.4. Thirty fractions (~1 ml) were collected, measured for protein concentration by absorbance at 280 nm and stored at −80° C. until further use. Consecutive protein-containing fractions were pooled pairwise and evaluated for their effect on etoposide (cytotoxic drug) induced caspase 3/7 activity in bovine tail disc NP cells as described below. Bioactive fractions were defined as protein fractions showing a decrease in caspase 3/7 activity in bovine NP cells on treatment with etoposide. These bioactive fractions were later analyzed for identification of proteins using mass-spectroscopy.

Bioactive fractions were reduced with dithiothreitol (DTT), the free cysteine residues alkylated with iodoacetamide and digested overnight with modified bovine trypsin (Promega, Madison, USA). The tryptic peptides were desalted and loaded onto a 50 cm×75 μm ID column containing RSLC 2 μm C18 packing material (EASY-Spray, Thermo-Fisher, Odense, Denmark) with an integrated emitter. The peptides were eluted into a Q-Exactive hybrid mass spectrometer (Thermo-Fisher, San Jose, Calif.) using an Easy-Spray nLC 1000 chromatography system (Thermo-Fisher, Odense Denmark) with a 90-minute gradient from 0% to 35% acetonitrile in 0.1% formic acid. The mass spectrometer was operated in a data dependent mode with 1 MS followed by 10 MS/MS spectra. The MS was acquired with a resolution of 70,000 FWHM, a target of $1\times10^6$ ions and a maximum scan time of 120 ms. The MS/MS scans were acquired with a resolution of 17,500 FWHM, a target of $1\times10^6$ ions and a maximum scan time of 120 ms using a relative collision energy of 27%. A dynamic exclusion time of 15 seconds was used for the MS/MS scans. The raw data files were acquired with XCalibur 2.2 (Thermo-Fisher Scientific) and processed with the Sequest search engine (Thermo-Fisher Scientific) using the UniProt canine database Aug. 12, 2014 version with 28,460 entries and with X!-Tandem (Beavis Informatics, Winnipeg, MAN). The processed data was imported into Scaffold 3.2 (Proteome Software, Portland, Oreg.). Peptides were considered to be identified if the Scaffold score exceeded the 0.1% false discovery rate (FDR) as determined by searching against the reversed UniProt canine database.

Bovine caudal disc NPs were obtained from six 3-year old steers. Human degenerative disc nucleus pulposus cells were obtained from patients (n=4) undergoing discectomy or fusion surgery at Toronto Western Hospital, University Health Network, Toronto, (with informed consent).

12-week old female Wistar rats (Charles River Laboratories International, Inc., MA, USA) were used in order to develop a pre-clinical rodent model of DDD and to evaluate the therapeutic potential of NCCM, CTGF and TGFβ1 in these pre-clinical rodent models. Experiments were performed in accordance with the Guide for the Care and Use of Laboratory Animals, and the experimental protocols were approved by the ethics approval board of Toronto Western Hospital, Toronto, ON, Canada. The surgical procedure was as follows: Anesthesia was achieved using isofluorane (5 L/min plus 1 L/min $O_2$) and maintained at 3 L/min. Once deeply anaesthetized, the animal was affixed on a stereotactic procedure apparatus (Model 900, Kopf Instruments California USA) with nose cone inhalation. For animal experiments, the tail was shaved and prepped with isopropanol in a sterile manner. Fluoroscopy was used to visualize needle penetration and to ensure that the needle penetrated into the center of the NP. For disc injury, a 26-gauge (G), 35° beveled, 0.75 inches high needle (Hamilton Company, USA) mounted on a Hamilton syringe was used. The needle was advanced completely through the selected tail IVD to penetrate the full thickness inclusive of the annulus fibrosus on both sides of the disc. Confirmation of needle placement was made using fluoroscopy and maintained in position for 2 minutes, withdrawn halfway to the center of the NP and left there for 1 minute and then slowly withdrawn completely over a 1-minute period. The animals were then removed from the stereotactic apparatus and allowed to recover in a warmed cage. At the end of study period i.e. 72 hrs-10 weeks, animals were humanely euthanized using $CO_2$ and each vertebral lumbar/caudal motion segment was dissected aseptically. IVDs were either fixed in formalin for histological analysis or the nucleus pulposus (healthy/injured) was harvested and lysed in RIPA buffer (50 mM Tris, pH=7.4, 150 mM NaCl, 1% NP-40 and protease inhibitor cocktail) for western blotting.

To determine the regenerative potential of NCCM, CTGF or TGFβ1, 4 IVDs per animal of 12 week old rats were injured using a 26 G needle as described above. Four weeks post-injury, animals were randomized into groups of six and an intra-discal injection (~8 μL) of either NCCM, CTGF (100 ng/mL) or TGFβ1 (10 ng/mL) was given under local anesthesia. For NCCM injected animals, the control group consisted of animals that received an intra-discal injection (~8 μL) of Hybridoma culture medium only, while phosphate buffered saline (PBS, 1×, pH=7.2) served as control for CTGF and TGFβ1 injected animal groups. Six weeks later, the NPs from injured and control discs were harvested and either fixed in formalin for histological analysis or lysed in RIPA lysis buffer for western blotting. Each of this experiment was repeated independently to ensure reproducibility.

Cell Signaling Technology Sampler kits including rabbit polyclonal/monoclonal antibodies for phospho-p42/p44 (Thr202/Tyr204), phospho-p38 (Thr180/Tyr182), phospho-cRaf (Ser338), total p42/p44, p38MAPK proteins were obtained from New England Biolabs Ltd. (Ontario, Canada). Rabbit polyclonal antibodies for Collagen 2 (ab34712), MMP-13 (ab39012), Cox2 (ab15191), Oct4 (ab18976), Nanog (ab106465), CTGF (ab6995), STAT3 (ab7966), rabbit monoclonal for MMP-3 (ab52915) and mouse monoclonal antibodies for Galectin 3 (ab2785) and β-actin (ab6276) were purchased from Abcam Inc. (Toronto, Canada). Goat polyclonal Brachyury antibody (sc-17743) and rabbit polyclonal antibodies for Aggrecan (sc-25674), TIMP-1 (sc-5538), ADAMTS-4 (sc-25582), TNFα(sc-8301), TGFβ1 (sc-146) and mouse monoclonal WISP2 (sc-514070) were obtained from Santa Cruz Biotechnology Inc. (CA, USA). Specific inhibitors targeting p42/44 (U0126), p38MAPK (SB203580), NFκB (BAY-11-7082), PI3K (Wortamanin), JAK1 inhibitor and STAT3 inhibitor were purchased from EMD Millipore (Ontario, Canada). Human recombinant IL-1β, TNFα, CTGF, WISP2 and TGFβ1 proteins were purchased from Peprotech Inc. (Quebec, Canada).

The tissues were fixed in 10% formalin and decalcified in 10% EDTA solution. The decalcified disc was initially split in the mid sagittal plane, embedded in paraffin and 5p thick sections were obtained for histological evaluation. Hemaetoxylin and eosin (H&E) and Safranin-O staining was performed to assess general morphology and proteoglycan content in these tissue sections as previously described[16]. For immunohistochemistry/immunofluorescence (IF), paraffin-embedded sections (5 μm) of human degenerative disc NP, bovine NP, healthy canines (NCD) and rat (healthy/injured) discs were deparaffinized in xylene, hydrated in gradient alcohol followed by antigen retrieval in Tris-EDTA buffer (pH=9.0). The sections were incubated with hydrogen peroxide (0.3% v/v) in methanol for 15 minutes to quench the endogenous peroxidase activity, followed by blocking with 10% serum to preclude non-specific binding. Thereafter, the slides were incubated with either rabbit or goat polyclonal/mouse monoclonal primary antibodies overnight (O/N) at 4° C. Protein expression was detected using respective secondary antibodies (rabbit/goat/mouse) from Vectastain ABC kit and diaminobenzidine (DAB) as a chromogen. In negative controls, the primary antibody was replaced by isotype-matched IgG. The bright field sections were evaluated by light microscopic examination using a ScanScope XT, Aperio Whole Slide Scanner available at Advanced Optical Microscopy Facility (AOMF), Toronto Medical Discovery (TMDT). Images were analyzed using Aperio ImageScope (version 10). For immunofluorescence, primary antibodies were detected using Alexa fluor (488/568 nm) labeled respective secondary antibodies (rabbit/goat/mouse, Invitrogen, Life Technologies, CA, USA). The sections were counterstained with DAPI and mounted with Fluoromount (Sigma-Aldrich, USA) mounting media. All images were acquired using Fluoview 1000 inverted microscope (Olympus IX81, Olympus) available at AOMF, Toronto Medical Discovery (TMDT). Images were analyzed using Fluoview1000 (Version 3.1) software.

After euthanasia, healthy rat lumbar/caudal spine IVDs, injured tail discs and bovine caudal IVD NPs were removed aseptically and the nucleus pulposus (NP) was removed separately and enzymatically digested according to methods established by the present inventors[16]. Similarly, human degenerative disc NPs were enzymatically digested using Pronase (0.4%, 1 hr at 37° C.) followed by Collagenase II treatment (0.015%, O/N, 37° C.). The following day, the cells were filtered with a 70μ cell strainer and cultured within a hypoxic incubator (NuAire, Minn., USA) in 3.5% $O_2$, 5%

$CO_2$, in Advanced Dulbecco's modified Eagle's medium (ADMEM) supplemented with 8% fetal bovine serum (FBS) and penicillin and streptomycin (100 U/mL). For treatments, the cells were either cultured in serum free ADMEM (no treatment controls) or treated with interleukin-1β (IL-1β, 10 ng/mL), tumor necrosis factor-alpha (TNFα, 50 ng/mL), connective tissue growth factor (CTGF, 10-100 ng/mL), Wnt-inducible soluble protein 2 (WISP2, 10-100 ng/mL) or transforming growth factor beta 1 (TGFβ1, 5-20 ng/mL) for various time points under hypoxic conditions.

Equal amounts of whole cell or tissue lysates prepared using RIPA lysis buffer were subjected to Western blotting as described earlier[18,19]. Total lysates (30 µg) were resolved on 10% sodium dodecyl sulphate-polyacrylamide gels (SDS-PAGE) under reducing conditions and then proteins were electro-transferred onto polyvinylidenedifluoride (PVDF) membranes (BioRad, Calif.). After blocking with 5% non-fat powdered milk in Tris-buffered saline (TBS, 0.1 M, pH=7.4), blots were incubated with rabbit or goat polyclonal/mouse monoclonal primary antibodies at 4° C. overnight. Membranes were washed three times with Tween (0.1%)-Tris-buffer saline (TTBS) and then incubated for 2 hrs at room temperature (RT) with the respective HRP-conjugated anti-IgG secondary antibodies (BioRad, Calif.), diluted as per the manufacturers suggestions in 2% non-fat milk in TBS (pH=7.2, 1×). Blots were washed three times with TTBS for 15 minutes and protein bands were detected by the enhanced chemiluminescence method (BioRad, Calif.) on Kodak Hyperfilm.

Nucleus pulposus cells (rat, bovine and human) were plated in 96-well flat bottom plates in order to evaluate the effect of treatment with growth factors in cell viability and proliferation assays. Rat NP cells were treated with CTGF, WISP-2 and TGFβ1 in a dose (1 ng/mL-100 ng/mL) and time dependent manner (24 hrs-96 hrs) to determine the optimum dose and time for the assessment of these growth factors on viability. Cell viability was determined using 3-(4,5-dimethylthiazol-2-yl)-2,5-diphenyltetrazolium bromide (MTT, Sigma-Aldrich, USA) as previously described[44]. A BrdU-ELISA (colorimetric) assay (Cat #ab126556, Abcam) was used for determining the effect of treatment with CTGF or TGFβ1 on human and rat NP cells (healthy/injured) following the manufacturer's instructions. Briefly, NP cells were treated with CTGF or TGFβ1 alone or in combination for 48 hrs following addition of BrdU reagent O/N in each well. Incorporated BrdU in DNA of proliferating cells was determined using anti-BrdU antibody and quantified by ELISA as per the manufacturer's instructions.

Apoptosis induced in NP cells (rat and human) as result of treatment with pro-inflammatory cytokines (IL-1β and TNFα) was determined using Caspase 3/7 and Caspase 9 specific Lumi-Glo assays (Promega, Madison). Briefly, NP cells were plated and treated with either IL-1β alone or in combination with TNFα only or in presence of CTGF and TGFβ1 for 48 hrs, followed by addition of specific reagents for Caspase 3/7 and Caspase 9 as per the manufacturer's instructions. Cells were incubated for another 4 hrs at 37° C., and plates were read in a multi-well luminescence plate reader.

Total RNA from healthy and treated (IL-1β alone or in combination with TNFα) rat NP cells, were isolated using RNAeasy extraction kit (Cat #74134, Qiagen) and quantified using a Nanodrop spectrophotometer. Total RNA (~400 ng) was reverse-transcribed using $RT^2$ First Strand Kit (Cat #330401, Qiagen) following the manufacturer's instructions for preparing cDNA. To evaluate the effect of IL-1β alone or in combination with TNFα on extra-cellular matrix (ECM) genes in rat NP cells, the $RT^2$ Profiler™ PCR Array Rat Extracellular Matrix & Adhesion Molecules (PARN-013Z, Qiagen) was used and compared with no treatment controls (NTC) in 3 independent experiments using real time PCR performed on ABI 7900 HT 384-well Fast block machine. Data analysis including calculation of ΔΔCt values, fold changes and p-values was carried out using software available online (https://www.qiagen.com/ca). Total RNA was isolated from human degenerative disc NP cells (H1/H2) treated with CTGF, TGFβ1, CTGF+TGFβ1 to evaluate their effect on collagen 2, HAPLN1, versican and thrombospondin 1 using gene specific primers. Similarly, RNA was isolated from human NP cells were treated with IL-1β alone or in combination TNFα in presence of CTGF and TGFβ1 to determine their effect on Cox2 and MMP-13 expression using qRT-PCR.

All data are expressed as means±SD. Significant differences in test and no treatment controls were determined using the paired Student's t-test. Statistical analysis was performed using the Graphpad Prism. $p<0.05$ was defined as statistically significant for all tests.

Preparation of Exemplary Compositions

To a tube containing 30 ml 1× phosphate buffered saline (PBS) solution was added 0.048 g of carboxymethylcellulose (cat #419273, Sigma) by sprinkling. This tube was shaken for 2-3 hours at room temperature while wrapped in aluminum foil. 0.384 g of dextrose (cat #D8066, Sigma) was then added. 0.384 g of glucosamine hydrochloride (cat #G1514, Sigma) was then added. 72 mg of chondroitin sulphate (cat #C4384, Sigma) was then added, and any clumps of material were dispersed and dissolved using a 1 ml sterile plastic tip; this tube was then shaken until everything was dissolved. pH was adjusted with 1.0N NaOH to pH 7.4, forming a "DRS stock solution".

To make a "DRS working solution", a 1:10 dilution of DRS stock solution was made in 1×PBS, filtered through a 0.22 um syringe filter in a biosafety cabinet and stored in 4 degrees C.

To make a "CTGF stock solution", CTGF was purchased from Peprotech Inc. (cat #120-19). 20 ug of lyophilized CTGF was centrifuged and dissolved with 1 ml of sterile deionized water.

To make a "CTGF working solution" in DRS, 5 ul of CTGF stock solution was added to 995 ul of DRS working solution resulting in 100 ng/ml of CTGF.

To make a "TGF-beta1 stock solution", TGF-beta1 was purchased from Peprotech Inc. (cat #100-21). 10 ug of lyophilized TGF-beta1 was centrifuged and dissolved with 1 ml of sterile 10 mM citric acid (pH approx. 3.0).

To make a "CTGF+TGF-beta1 working solution in DRS", which had the most significant effects in the FIGS. presented, 1 ul of the TGF-beta1 stock solution, 5 ul of the CTGF stock solution, and 994 ul of the DRS stock solution was mixed and aliquoted into four tubes of 250 ul each.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

1. Global Burden of Disease Study 2013 Collaborators. Global, regional, and national incidence, prevalence, and years lived with disability for 301 acute and chronic diseases and injuries in 188 countries, 1990-2013: a systematic analysis for the Global Burden of Disease Study 2013. *Lancet* 386, 743-800 (2015).
2. Hoy, D et al. The global burden of low back pain: estimates from the Global Burden of Disease 2010 study. *Ann. Rheum. Dis.* 73, 968-74 (2014).
3. Risbud M V, Schaer T P, Shapiro I M. Toward an understanding of the role of notochordal cells in the adult intervertebral disc: from discord to accord. *Dev. Dyn.* 239, 2141-8 (2010).
4. Risbud M V, Shapiro I M. Notochordal cells in the adult intervertebral disc: new perspective on an old question. *Crit. Rev. Eukaryot. Gene. Expr.* 21, 29-41 (2011).
5. Pattappa, G et al. Diversity of intervertebral disc cells: phenotype and function. *J. Anat.* 221, 480-96 (2012).
6. Phillips F M, Slosar P J, Youssef J A, Andersson G, Papatheofanis F. Lumbar spine fusion for chronic low back pain due to degenerative disc disease: a systematic review. *Spine* (Phila Pa. 1976). 38, E409-22 (2013).
7. Bydon, M et al. Lumbar fusion versus non-operative management for treatment of discogenic low back pain: a systematic review and meta-analysis of randomized controlled trials. *J. Spinal. Disord. Tech.* 27, 297-304 (2014).
8. Ren C, Song Y, Liu L, Xue Y. Adjacent segment degeneration and disease after lumbar fusion compared with motion-preserving procedures: a meta-analysis. *Eur. J. Orthop. Surg. Traumatol.* 24, S245-53 (2014).
9. Masuda K. Biological repair of the degenerated intervertebral disc by the injection of growth factors. *Eur. Spine J.* 17, 441-51 (2008).
10. Wang S Z, Rui Y F, Lu J, Wang C. Cell and molecular biology of intervertebral disc degeneration: current understanding and implications for potential therapeutic strategies. *Cell. Prolif.* 47, 381-90 (2014).
11. Nishida, K et al. Gene therapy approach for disc degeneration and associated spinal disorders. Eur. Spine. J. 17, 459-66 (2008).
12. Wang S Z, Rui Y F, Tan Q, Wang C. Enhancing intervertebral disc repair and regeneration through biology: platelet-rich plasma as an alternative strategy. *Arthritis. Res. Ther.* 15, 220 (2013).
13. Sakai D, Andersson G B. Stem cell therapy for intervertebral disc regeneration: obstacles and solutions. *Nat. Rev. Rheumatol.* 11, 243-56 (2015).
14. Wang, Z et al. Efficacy of intervertebral disc regeneration with stem cells—a systematic review and meta-analysis of animal controlled trials. *Gene* 564, 1-8 (2015).
15. Kandel R, Roberts S, Urban J P. Tissue engineering and the intervertebral disc: the challenges. *Eur. Spine. J.* 17, 480-91 (2008).
16. Bergknut, N et al. Intervertebral disc degeneration in the dog. Part 1: Anatomy and physiology of the intervertebral disc and characteristics of intervertebral disc degeneration. *Vet. J.* 195, 282-91 (2013).
17. Smolders, L A et al. Intervertebral disc degeneration in the dog. Part 2: chondrodystrophic and non-chondrodystrophic breeds. *Vet. J.* 195, 292-9 (2013).
18. Erwin W M, Ashman K, O'Donnel P, Inman R D. Nucleus pulposus notochord cells secrete connective tissue growth factor and up-regulate proteoglycan expression by intervertebral disc chondrocytes. *Arthritis. Rheum.* 54, 3859-67 (2006).
19. Erwin W M, Islam D, Inman R D, Fehlings M G, Tsui F W. Notochordal cells protect nucleus pulposus cells from degradation and apoptosis: implications for the mechanisms of intervertebral disc degeneration. *Arthritis. Res. Ther.* 13, R215 (2011).
20. Mehrkens, A et al. Canine notochordal cell-secreted factors protect murine and human nucleus pulposus cells from apoptosis by inhibition of activated caspase-9 and caspase-3/7. *Evid. Based. Spine. Care. J.* 4, 154-6 (2013).
21. Bach, F C et al. The species-specific regenerative effects of notochordal cell-conditioned medium on chondrocyte-like cells derived from degenerated human intervertebral discs. *Eur. Cell. Mater.* 30, 132-47 (2015).
22. de Vries, S A et al. Conditioned medium derived from notochordal cell-rich nucleus pulposus tissue stimulates matrix production by canine nucleus pulposus cells and bone marrow-derived stromal cells. *Tissue. Eng. Part. A.* 21, 1077-84 (2015).
23. Korecki C L, Taboas J M, Tuan R S, Iatridis J C. Notochordal cell conditioned medium stimulates mesenchymal stem cell differentiation toward a young nucleus pulposus phenotype. *Stem. Cell. Res. Ther.* 1, 18 (2010).
24. Cornejo M C, Cho S K, Giannarelli C, Iatridis J C, Purmessur D. Soluble factors from the notochordal-rich intervertebral disc inhibit endothelial cell invasion and vessel formation in the presence and absence of pro-inflammatory cytokines. *Osteoarthritis. Cartilage.* 23, 487-96 (2015).
25. Singh K, Masuda K, An H S. Animal models for human disc degeneration. *Spine. J.* 5, 267S-279S (2005).
26. Alini, M et al. Are animal models useful for studying human disc disorders/degeneration? *Eur. Spine. J.* 17, 2-19 (2008).
27. Sivan, S S et al. Biochemical composition and turnover of the extracellular matrix of the normal and degenerate intervertebral disc. *Eur. Spine. J.* 23, S344-53 (2014).
28. Risbud M V, Shapiro I M. Role of cytokines in intervertebral disc degeneration: pain and disc content. *Nat. Rev. Rheumatol.* 10, 44-56 (2014).
29. Millward-Sadler S J, Costello P W, Freemont A J, Hoyland J A. Regulation of catabolic gene expression in normal and degenerate human intervertebral disc cells: implications for the pathogenesis of intervertebral disc degeneration. *Arthritis. Res. Ther.* 11, R65 (2009).
30. Vergroesen, P P et al. Mechanics and biology in intervertebral disc degeneration: a vicious circle. *Osteoarthritis. Cartilage.* 23, 1057-70 (2015).
31. Galbusera, F et al. Ageing and degenerative changes of the intervertebral disc and their impact on spinal flexibility. *Eur. Spine. J.* 23, S324-32 (2014).
32. Phillips K L, Jordan-Mahy N, Nicklin M J, Le Maitre C L. Interleukin-1 receptor antagonist deficient mice provide insights into pathogenesis of human intervertebral disc degeneration. *Ann. Rheum. Dis.* 72, 1860-7 (2013).
33. Gorth, D J et al. IL-1ra delivered from poly(lactic-co-glycolic acid) microspheres attenuates IL-1β-mediated degradation of nucleus pulposus in vitro. *Arthritis. Res. Ther.* 14, R179 (2012).
34. Goupille P, Mulleman D, Chevalier X. Is interleukin-1 a good target for therapeutic intervention in intervertebral disc degeneration: lessons from the osteoarthritic experience. *Arthritis. Res. Ther.* 9, 110 (2007).
35. Le Maitre C L, Hoyland J A, Freemont A J. Interleukin-1 receptor antagonist delivered directly and by gene therapy inhibits matrix degradation in the intact degenerate human intervertebral disc: an in situ zymographic and gene therapy study. *Arthritis. Res. Ther.* 9, R83 (2007).

36. Le Maitre C L, Freemont A J, Hoyland J A. A preliminary in vitro study into the use of IL-1 Ra gene therapy for the inhibition of intervertebral disc degeneration. *Int. J. Exp. Pathol.* 87, 17-28 (2006).
37. Sinclair, S M et al. Attenuation of inflammatory events in human intervertebral disc cells with a tumor necrosis factor antagonist. *Spine* (Phila Pa. 1976). 36, 1190-6 (2011).
38. Studer, R K et al. p38 MAPK inhibition in nucleus pulposus cells: a potential target for treating intervertebral disc degeneration. *Spine* (Phila Pa. 1976). 32, 2827-33 (2007).
39. Cao, C et al. Bone marrow mesenchymal stem cells slow intervertebral disc degeneration through the NF-κB pathway. *Spine. J.* 15, 530-8 (2015).
40. Jin, H et al. TGF-β signaling plays an essential role in the growth and maintenance of intervertebral disc tissue. *FEBS. Lett.* 585, 1209-15 (2011).
41. Nishida, K et al. Modulation of the biologic activity of the rabbit intervertebral disc by gene therapy: an in vivo study of adenovirus-mediated transfer of the human transforming growth factor beta 1 encoding gene. *Spine* (Phila Pa. 1976). 24, 2419-25 (1999).
42. Yang, H et al. TGF-β antagonizes TNF-α induced up-regulation of matrix metalloproteinase 3 in nucleus pulposus cells: role of the ERK1/2 pathway. *Connect. Tissue. Res.* 29, 1-8 (2015).
43. Tolonen, J et al. Growth factor expression in degenerated intervertebral disc tissue. An immunohistochemical analysis of transforming growth factor beta, fibroblast growth factor and platelet-derived growth factor. *Eur. Spine. J.* 15, 588-96 (2006).
44. Matta A, DeSouza L V, Ralhan R, Siu K W. Small interfering RNA targeting 14-3-3ζ increases efficacy of chemotherapeutic agents in head and neck cancer cells. *Mol. Cancer. Ther.* 9, 2676-88 (2010).

The invention claimed is:

1. A pharmaceutical composition for treating degeneration of the intervertebral disc (IVD), comprising:
    i) chondroitin or chondroitin sulfate at a concentration of about 0.024% to about 2% by weight of the composition;
    ii) glucosamine or glucosamine hydrochloride at a concentration of about 0.126% to about 25% by weight of the composition;
    iii) connective tissue growth factor (CTGF) at a concentration of about 50 ng/mL to about 500 ng/mL of the composition as the sole growth factor in the composition;
    transforming growth factor beta 1 (TGFβ1) at a concentration of about 1 ng/mL to about 100 ng/mL of the composition as the sole growth factor in the composition; or
    CTGF at a concentration of about 50 ng/mL to about 500 ng/mL of the composition and TGFβ1 at a concentration of about 1 ng/mL to about 100 ng/mL of the composition as the only growth factors in the composition,
    wherein the composition is suitable for IVD injection, and
    wherein the composition promotes regeneration of a degenerative IVD nucleus pulposus (NP) and/or increases viability of degenerative disc NP cells.
2. The composition of claim 1, wherein the composition comprises the chondroitin sulfate and/or the glucosamine hydrochloride.
3. The composition of claim 2, wherein the composition comprises the chondroitin sulfate.
4. The composition of claim 3, wherein the chondroitin sulfate is present at up to about 0.5% by weight of the composition.
5. The composition of claim 3, wherein the chondroitin sulfate is present at about 0.024% by weight of the composition.
6. The composition of claim 2, wherein the composition comprises the glucosamine hydrochloride.
7. The composition of claim 6, wherein the glucosamine hydrochloride is present at up to about 1.5% by weight of the composition.
8. The composition of claim 6, wherein the glucosamine hydrochloride is present at up to about 5% by weight of the composition.
9. The composition of claim 6, wherein the glucosamine hydrochloride is present at up to about 20% by weight of the composition.
10. The composition of claim 6, wherein the glucosamine hydrochloride is present at about 0.126% by weight of the composition.
11. The composition of claim 1, wherein the composition comprises the CTGF, at a concentration of about 50 ng/mL, about 75 ng/mL, about 100 ng/mL, about 125 ng/mL, about 150 ng/mL, about 175 ng/mL, about 200 ng/mL, about 225 ng/mL, about 250 ng/mL, about 275 ng/mL, about 300 ng/mL, about 325 ng/ml, about 350 ng/mL, about 375 ng/mL, about 400 ng/mL, about 425 ng/mL, about 450 ng/mL, about 475 ng/mL, or about 500 ng/mL, of the composition.
12. The composition of claim 1, wherein the composition comprises the TGFβ1, at a concentration of about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, or about 100 ng/mL, of the composition.
13. The composition of claim 1, wherein, if present, the chondroitin, the chondroitin sulfate, the glucosamine and the glucosamine hydrochloride are in the form of a solution.
14. The composition of claim 1, further comprising carboxymethylcellulose (CMC).
15. The composition of claim 14, wherein the CMC is present at no more than about 0.5% by weight of the composition.
16. The composition of claim 1, further comprising one or more sugar.
17. The composition of claim 1, further comprising a buffer.
18. The composition of claim 17, wherein the buffer is in a quantity sufficient to stabilize the pH of the composition at about 6 to about 7.
19. The composition of claim 1, further comprising water.
20. The composition of claim 1, wherein the composition comprises the chondroitin sulfate, the glucosamine hydrochloride, the CTGF, and the TGFβ1.
21. The composition of claim 1, wherein the composition comprises the chondroitin sulfate, the glucosamine hydrochloride, and the CTGF.
22. The composition of claim 1, wherein the composition comprises the chondroitin sulfate, the glucosamine hydrochloride, and the TGFβ1.
23. The composition of claim 1, wherein the composition comprises: the chondroitin sulfate, the glucosamine or glucosamine hydrochloride; the CTGF; and the TGFβ1.

24. The composition of claim 1, wherein the composition comprises: the chondroitin sulfate; the glucosamine or glucosamine hydrochloride; and the CTGF.

25. The composition of claim 1, wherein the composition comprises: the chondroitin sulfate, the glucosamine or glucosamine hydrochloride; and the TGFβ1.

26. The composition of claim 1, wherein the composition comprises: the chondroitin or chondroitin sulfate; the glucosamine hydrochloride; the CTGF; and the TGFβ1.

27. The composition of claim 1, wherein the composition comprises: the chondroitin or chondroitin sulfate; the glucosamine hydrochloride; and the CTGF.

28. The composition of claim 1, wherein the composition comprises: the chondroitin or chondroitin sulfate; the glucosamine hydrochloride; and the TGFβ1.

29. The composition of claim 1, wherein the composition comprises:
   (i) the CTGF at a concentration of about 100 ng/mL;
   (ii) the TGβ1 at a concentration of about 10 ng/mL; and
   (iii) the chondroitin sulfate and the glucosamine hydrochloride.

* * * * *

UNITED STATES PATENT AND TRADEMARK OFFICE
CERTIFICATE OF CORRECTION

PATENT NO. : 11,471,480 B2
APPLICATION NO. : 17/358731
DATED : October 18, 2022
INVENTOR(S) : William Mark Erwin et al.

It is certified that error appears in the above-identified patent and that said Letters Patent is hereby corrected as shown below:

In the Claims

At Column 23, Claim number 1, Line numbers 43-45, read:
"ii) glucosamine or glucosamine hydrochloride at a concentration of about 0.126% to about 25% by weight of the composition;"

Should read:
-- ii) glucosamine or glucosamine hydrochloride at a concentration of about 0.126% to about 25% by weight of the composition; and --

Signed and Sealed this
Eighteenth Day of March, 2025

Coke Morgan Stewart
*Acting Director of the United States Patent and Trademark Office*